United States Patent
Chen et al.

(10) Patent No.: US 9,464,078 B2
(45) Date of Patent: Oct. 11, 2016

(54) MONOHYDRATE OF AZAADAMANTANE DERIVATIVES

(75) Inventors: Shuang Chen, Gurnee, IL (US); James J. Napier, Antioch, IL (US); Geoff G. Z. Zhang, Vernon Hills, IL (US); Paul J. Brackemeyer, Mount Prospect, IL (US)

(73) Assignee: AbbVie Inc., North Chicago, IL (US)

( * ) Notice: Subject to any disclaimer, the term of this patent is extended or adjusted under 35 U.S.C. 154(b) by 175 days.

(21) Appl. No.: 13/238,239

(22) Filed: Sep. 21, 2011

(65) Prior Publication Data

US 2012/0245195 A1   Sep. 27, 2012

Related U.S. Application Data

(60) Provisional application No. 61/385,674, filed on Sep. 23, 2010.

(51) Int. Cl.
| | |
|---|---|
| *A61K 31/44* | (2006.01) |
| *C07D 471/08* | (2006.01) |
| *C07D 451/14* | (2006.01) |
| *A61K 31/439* | (2006.01) |
| *A61K 45/06* | (2006.01) |

(52) U.S. Cl.
CPC ........... *C07D 451/14* (2013.01); *A61K 31/439* (2013.01); *A61K 45/06* (2013.01); *C07D 471/08* (2013.01)

(58) Field of Classification Search
None
See application file for complete search history.

(56) References Cited

U.S. PATENT DOCUMENTS

| | | | |
|---|---|---|---|
| 4,578,382 A | 3/1986 | Jarreau et al. | |
| 4,816,453 A | 3/1989 | Watts | |
| 4,950,759 A | 8/1990 | van Wijngaarden et al. | |
| 4,985,424 A | 1/1991 | van Wijngaarden et al. | |
| 5,260,303 A | 11/1993 | Becker et al. | |
| 5,280,028 A | 1/1994 | Flynn et al. | |
| 5,385,912 A | 1/1995 | Neuenschwander et al. | |
| 5,399,562 A | 3/1995 | Becket et al. | |
| 5,434,151 A | 7/1995 | Cai et al. | |
| 5,591,749 A | 1/1997 | Becker et al. | |
| 5,604,239 A | 2/1997 | Becker et al. | |
| 5,643,917 A | 7/1997 | Flynn et al. | |
| 5,723,472 A | 3/1998 | Miyazawa et al. | |
| 5,840,903 A | 11/1998 | Flynn et al. | |
| 5,852,037 A | 12/1998 | Bodick et al. | |
| 5,952,339 A | 9/1999 | Bencherif et al. | |
| 5,986,100 A | 11/1999 | Crooks et al. | |
| 6,057,446 A | 5/2000 | Crooks et al. | |
| 6,093,724 A | 7/2000 | Grewal et al. | |
| 6,251,916 B1 | 6/2001 | Grewal et al. | |
| 6,277,870 B1 | 8/2001 | Gurley et al. | |
| 6,323,194 B1 | 11/2001 | Grewal et al. | |
| 6,417,359 B1 | 7/2002 | Crooks et al. | |
| 6,423,842 B1 | 7/2002 | Grewal et al. | |
| 6,555,550 B1 | 4/2003 | Grewal et al. | |
| 6,627,648 B1 | 9/2003 | Dull et al. | |
| 6,861,443 B2 | 3/2005 | Gurley et al. | |
| 6,890,922 B2 | 5/2005 | Niewohner et al. | |
| 7,018,797 B2 | 3/2006 | Reitz et al. | |
| 7,067,261 B2 | 6/2006 | Bencherif et al. | |
| 7,112,593 B2 | 9/2006 | Okada et al. | |
| 7,122,540 B2 | 10/2006 | Niewohner et al. | |
| 7,135,454 B2 | 11/2006 | Chimienti et al. | |
| 7,253,196 B2 | 8/2007 | Henriksson et al. | |
| 7,652,010 B2 | 1/2010 | Peters et al. | |
| 7,691,808 B2 | 4/2010 | Chimienti et al. | |
| 7,696,206 B2 | 4/2010 | Niewohner et al. | |
| 7,704,997 B1 | 4/2010 | Carroll et al. | |
| 7,704,999 B2 | 4/2010 | Niewohner et al. | |
| 7,718,677 B2 | 5/2010 | Quik et al. | |
| 7,723,367 B2 | 5/2010 | Carroll et al. | |
| 7,732,163 B2 | 6/2010 | O'Brien et al. | |
| 7,763,725 B2 | 7/2010 | Poitout et al. | |
| 7,807,700 B2 | 10/2010 | Henriksson et al. | |
| 7,981,906 B2 | 7/2011 | Dull et al. | |
| 8,217,067 B2 | 7/2012 | Carroll et al. | |
| 2004/0185468 A1 | 9/2004 | Leonard et al. | |
| 2004/0209886 A1 | 10/2004 | Salvati et al. | |
| 2005/0043347 A1 | 2/2005 | Betschmann et al. | |
| 2005/0065178 A1 | 3/2005 | Basha et al. | |
| 2005/0101602 A1 | 5/2005 | Basha et al. | |
| 2006/0052374 A1 | 3/2006 | Carroll et al. | |
| 2008/0153806 A1 | 6/2008 | Peters et al. | |
| 2008/0167336 A1* | 7/2008 | Schrimpf et al. | ............. 514/294 |
| 2009/0093403 A1 | 4/2009 | Zhang et al. | |
| 2009/0099038 A1 | 4/2009 | Deisseroth et al. | |
| 2009/0118326 A1 | 5/2009 | Jiang et al. | |
| 2009/0148525 A1 | 6/2009 | Cowen | |
| 2009/0239901 A1 | 9/2009 | Bencherif | |

(Continued)

FOREIGN PATENT DOCUMENTS

| | | |
|---|---|---|
| CA | 2736871 | 3/2010 |
| EP | 0088484 | 9/1983 |

(Continued)

OTHER PUBLICATIONS

Han (Advances in Characterization of Pharmaceutical Hydrates. Trends in Bio/Pharmaceutical Industry, pp. 25-29. Mar. 2006).*
Non-Final Office Action mailed Apr. 23, 2014 for U.S. Appl. No. 13/653,192, filed Oct. 16, 2012.
Burger., "Principles and Practice" in: Medicinal Chemistry and Drug Discovery, 5th Edition, Wolff M.E., ed., John Wiley and Sons, 1994, pp. 975-977.
Costa Rican Opposition for Application No. 2013-0169 by Asociacion de la Industria Farmaceutica Nacional, filed Sep. 20, 2013 (with English Translation).
Greene T.W., et al., in: Protective Groups in Organic Synthesis, 3rd Edition, John Wiley and Sons, Inc., 1999, Preface, Table of Contents, Abbreviations.
Notice of Allowance mailed May 1, 2012 for U.S. Appl. No. 11/935,157, filed Nov. 5, 2007.
Notice of Allowance mailed Sep. 4, 2012 for U.S. Appl. No. 11/935,157, filed Nov. 5, 2007.

(Continued)

*Primary Examiner* — Jared Barsky
(74) *Attorney, Agent, or Firm* — Portia Chen

(57) ABSTRACT

The invention relates to a crystalline monohydrate of (4s)-4-(5-phenyl-1,3,4-thiadiazol-2-yloxy)-1-azatricyclo[3.3.1.1$^{3,7}$]decane dihydrogen citrate, compositions comprising such compound, and a process for preparing such compound.

3 Claims, 9 Drawing Sheets

(56) References Cited

U.S. PATENT DOCUMENTS

| | | |
|---|---|---|
| 2009/0291976 A1 | 11/2009 | Ferchmin et al. |
| 2009/0306075 A1 | 12/2009 | Mccoull et al. |
| 2009/0312372 A1 | 12/2009 | Mccoull et al. |
| 2010/0029723 A1 | 2/2010 | Quik et al. |
| 2010/0047795 A1 | 2/2010 | Leonard et al. |
| 2010/0105658 A1 | 4/2010 | Nagashima et al. |
| 2010/0130420 A1 | 5/2010 | Stemson et al. |
| 2010/0144538 A1 | 6/2010 | Belouchi et al. |
| 2010/0152108 A1 | 6/2010 | Hung et al. |
| 2010/0158895 A1 | 6/2010 | Quik et al. |
| 2010/0159004 A1 | 6/2010 | Quik et al. |
| 2010/0166735 A1 | 7/2010 | Quik et al. |
| 2010/0196463 A1 | 8/2010 | Quik et al. |
| 2010/0197740 A1 | 8/2010 | Wang et al. |
| 2010/0234349 A1 | 9/2010 | Olsen et al. |
| 2011/0034475 A1 | 2/2011 | Feuerbach et al. |
| 2011/0059947 A1 | 3/2011 | Bencherif et al. |
| 2011/0077276 A1 | 3/2011 | Quik et al. |
| 2011/0097324 A1 | 4/2011 | Liu |
| 2011/0098312 A1 | 4/2011 | Bencherif et al. |
| 2011/0124678 A1 | 5/2011 | Bencherif et al. |
| 2011/0136791 A1 | 6/2011 | Bergis et al. |

FOREIGN PATENT DOCUMENTS

| | | |
|---|---|---|
| EP | 0227215 | 7/1987 |
| EP | 0076755 | 4/1988 |
| EP | 0645391 | 3/1995 |
| EP | 0709381 | 5/1996 |
| EP | 0774256 | 5/1997 |
| EP | 1977746 | 10/2008 |
| EP | 2255848 | 12/2010 |
| EP | 2322166 | 5/2011 |
| EP | 2322167 | 5/2011 |
| EP | 2322168 | 5/2011 |
| JP | 2005232071 | 9/2005 |
| WO | WO 92/15579 | 9/1992 |
| WO | WO 92/15593 | 9/1992 |
| WO | WO 94/00454 | 1/1994 |
| WO | WO 94/02482 | 2/1994 |
| WO | WO 97/20819 | 6/1997 |
| WO | WO 98/27983 | 7/1998 |
| WO | WO 99/20757 | 4/1999 |
| WO | 9924433 A1 | 5/1999 |
| WO | WO 99/51601 | 10/1999 |
| WO | WO 99/51602 | 10/1999 |
| WO | WO 99/56745 | 11/1999 |
| WO | WO 99/62505 | 12/1999 |
| WO | WO 00/11001 | 3/2000 |
| WO | 00/66586 | 11/2000 |
| WO | WO 00/71520 | 11/2000 |
| WO | WO 01/40261 | 7/2001 |
| WO | 0182978 A2 | 11/2001 |
| WO | WO 02/02564 | 1/2002 |
| WO | WO 02/50045 | 6/2002 |
| WO | WO 02/076973 | 10/2002 |
| WO | 03/014732 | 2/2003 |
| WO | WO 03/044020 | 5/2003 |
| WO | WO 03/094831 | 11/2003 |
| WO | WO 2004/009577 | 1/2004 |
| WO | WO 2004/016608 | 2/2004 |
| WO | WO 2004/091646 | 10/2004 |
| WO | WO 2005/020921 | 3/2005 |
| WO | WO 2005/028477 | 3/2005 |
| WO | 2005047303 A2 | 5/2005 |
| WO | WO 2005/116002 | 12/2005 |
| WO | WO 2005/123732 | 12/2005 |
| WO | WO 2006/005608 | 1/2006 |
| WO | 2006010811 A1 | 2/2006 |
| WO | 2006012395 A2 | 2/2006 |
| WO | WO 2006/026469 | 3/2006 |
| WO | WO 2006/040352 | 4/2006 |
| WO | WO 2006/045716 | 5/2006 |
| WO | 2006065233 | 6/2006 |
| WO | WO 2007/024391 | 3/2007 |
| WO | 2007/038058 | 4/2007 |
| WO | WO 2007/065892 | 6/2007 |
| WO | WO 2008/002594 | 1/2008 |
| WO | WO 2008/020131 | 2/2008 |
| WO | WO 2008/028903 | 3/2008 |
| WO | WO 2008/051599 | 5/2008 |
| WO | WO 2008/053194 | 5/2008 |
| WO | WO 2008/058096 | 5/2008 |
| WO | WO 2008/096870 | 8/2008 |
| WO | WO 2008/112177 | 9/2008 |
| WO | 2008118742 A1 | 10/2008 |
| WO | WO 2008/122049 | 10/2008 |
| WO | WO 2009/017454 | 2/2009 |
| WO | WO 2009/018505 | 2/2009 |
| WO | WO 2009/018511 | 2/2009 |
| WO | 2009066735 A1 | 5/2009 |
| WO | WO 2009/058120 | 5/2009 |
| WO | WO 2009/071326 | 6/2009 |
| WO | WO 2009/102962 | 8/2009 |
| WO | WO 2009/140201 | 11/2009 |
| WO | WO 2009/149562 | 12/2009 |
| WO | WO 2010/030887 | 3/2010 |
| WO | WO 2010/042799 | 4/2010 |
| WO | WO 2010/056622 | 5/2010 |
| WO | WO 2010/088400 | 8/2010 |
| WO | 2011014817 A1 | 2/2011 |
| WO | WO 2011/022467 | 2/2011 |
| WO | WO 2011/044537 | 4/2011 |
| WO | 2011058582 A1 | 5/2011 |
| WO | 2012040404 A1 | 3/2012 |
| WO | 2012041476 A1 | 4/2012 |
| WO | 2012059932 A1 | 5/2012 |

OTHER PUBLICATIONS

Prescott D.M., "Methods in Cell Biology", Academic Press, 1976, Table of Contents.

Adams, C.E. et al., "Development of the α7 nicotinic cholinergic receptor in rat hippocampal formation," Developmental Brain Research (2002) 139:175-187.

Adler, L.E. et al., "Schizophrenia, Sensory Gating, and Nicotinic Receptors," Schizophrenia Bull. (1998) 24:189-202.

Banker, G.S. et al., Modern Pharmaceutics, 3rd Edition, Marcel Dekker, New York (1996) p. 451 and 596.

Becker, D.P. et al., "A Short Synthesis of 1-Azaadamantan-4-one and the 4r and 4s Isomers of 4-Amino- 1-azaadamantane," Synthesis (1992) 1080-1082.

Bitner, R. et al., "Alpha-7 nAChR-mediated regulation of GSK3 and tau phosphorylation: potential for disease modification in Alzheimer's disease," Soc. Neuroscience Abstract 325.6 (2006).

Bunnelle, W.H. et al., "Design of ligands for the nicotinic acetylcholine receptors: the quest for selectivity," Curr. Topics in Medicinal Chem. (2004) 4:299-334.

Bunnelle, W.H. et al., "Neuronal nicotinic acetylcholine receptor ligands as potential analgesics," Exp. Opin. Therapeutic Patents (2003) 13(7):1003-1021.

Cordero-Erausquin, M. et al., Proc. Natl. Acad. Sci. USA (2001) 98:2803-2807.

Eliel, E.L. et al., Stereochemistry of Organic Compounds, John Wiley & Sons, Inc., Table of Contents (1994) v-viii.

Falk, L. et al., "Higher expression of α7 nicotinic acetylcholine receptors in human fetal compared to adult brian," Developmental Brain Research (2003) 142:151-160.

Flynn, D.L. et al., "New Aza(NOR)adamantanes are agonists at the newly identified serotonin 5-HT4 receptor and antagonists at the 5-HT3 receptor," Biorg. Med. Chem. Lett. (1992) 2(12):1613-1618.

Friedman, J.I. et al., "A double blind placebo controlled trial of donepezil adjunctive treatement to risperidone for the cognitive impairment of schizophrenia," Biol. Psychiatry (2002) 51:349-357.

Furniss, B.S. et al., Vogel's Textbook of Practical Organic Chemistry, 5th Edition, Longman Scientific and Technical, Essex, England (Table of Contents) (1989) v-xvi.

Greene, T.W. et al., Chapter 7 "Protection for the amino group," Protective Groups in Organic Synthesis, 3rd Edition, John Wiley & Sons, New York, NY, (1999) 494-653.

(56) References Cited

OTHER PUBLICATIONS

Heeschen, C. et al., "A novel angiogenic pathway mediated by non-neuronal nicotinic acetylcholine receptors," J. Clin. Invest. (2002) 110:527-536.
Heeschen, C. et al., "Nicotine stimulates angiogenesis and promotes tumor growth and atherosclerosis," Nature Medicine (2001) 7(7):833-839.
Higuchi, T. et al., Pro-drugs as novel drug delivery systems, vol. 14 of the A.C.S. Symposium Series (1975).
Iriepa, I. et al., "Synthesis and structural study of a series of amides derived from 4α- and 4β-amino-1-azaadamantanes as potential 5-HT$_3$ receptor antagonists," J. Mol. Struct. (1999) 509:105-114.
IUPAC Commission on Nomenclature of Organic Chemistry, Rules for the Nomenclature of Organic Chemistry, Section E: Stereochemistry (Recommendations 1974), Pure Appl. Chem. (1976) 45:13-30.
Jacobi, J. et al., "Nicotine accelerates angiogenesis and wound healing in genetically diabetec mice," Am. J. Pathol. (2002) 161(1):97-104.
Jonnala, R.R. et al., "Relationship between the increased cell surface α7 nicotinic receptor expression and neuroprotection induced by several nicotinic receptor agonists," J. Neurosci. Res. (2001) 66:565-572.
Kihara, T. et al., "α7 Nicotinic receptor transduces signals to phosphatidylinositol 3-kinase to block A β-amyloid-induced neurotoxicity," J. Biol. Chem. (2001) 276(17):13541-13546.
Leonard, S., "Smoking and schizophrenia: abnormal nicotinic receptor expression," Eur. J. Pharmacol. (2000) 393:237-242.
Levin, E.D., "Nicotinic receptor subtypes and cognitive function," J. Neurobiol. (2002) 53:633-640.
Liu, Q. et al., "β-Amyloid peptide blocks the response of α7-containing nicotinic receptors on hippocampal neurons," Proc. Natl. Acad. Sci. USA (2001) 98(8):4734-4739.
Pabreza, L.A. et al., "[$^3$H]Cytisine binding to nicotinic cholinergic receptors in brain," Mol. Pharm. (1990) 39:9-12.
Paterson, D. et al., "Neuronal nicotinic receptors in the human brain," Progress in Neurobiology (2000) 61:75-111.
Prescott, editor, Methods in Cell Biology, vol. XIV, Academic Press, New York, NY (1976) 33-71.
Radek, R.J. et al., "α$_4$β$_2$ Nicotinic receptor stimulation contributes to the effects of nicotine in the DBA/2 mouse model of sensory gating," Psychopharmacology (Berl) (2006) 187:47-55.
Roche, E.B., editor, Bioreversible Carriers in Drug Design, American Pharmaceutical Association and Pergamon Press (1987).
Rowley, M. et al., "Current and novel approaches to the drug treatment of schizophrenia," J. Med. Chem. (2001) 44(4):477-501.
Sawa, A. et al., "Schizophrenia: Neural Mechangisms for Novel Therapies," Mol. Med. (2003) 9:3-9.
Schildan, A. et al., "Synthesis and evaluation of tritium labelled 10-methylgalanthamine iodide: a novel compound to examine the mechanism of interaction of galanthamine derivatives with the nicotinic acetylcholine receptors," J. Label Compd. Radiopharm. (2003) 46:1117-1125.
Shimohama, S. et al., "Nicotinic α7 receptors protect against glutamate neurotoxicity and neuronal ischemic damage," Brain Res. (1998) 779:359-363.
Son, J. et al., "Evidence suggesting that the mouse sperm acrosome reaction initiated by the zona pellucida involves an α7 nicotinic acetylcholine receptor[1]," Biol. Reprod. (2003) 68:1348-1353.
Stevens, K.E. et al., "Selective α7-nicotinic agonists normalize inhibition of auditory response in DBA mice," Psychopharmacology (1998) 136:320-327.
Stotter, P.L. et al., "Quinuclidine boranes as intermediates in formation and isolation of functionalized quinuclidine systems," Heterocycles (1987) 25:251-258.
Tsuneki, H. et al., "Mouse muscle devervation increases expression of an α7 nicotinic receptor with unusual pharmacology," J. Physiol. (London) (2003) 547:169-179.
Vachal, P. et al., "General facile synthesis of 2,5-diarylheteropentalenes," Tetrahedron Lett. (2004) 45:7157-7161.
Wang, H. et al., "Nicotinic acetylcholine receptor α7 subunit is an essential regulator of inflammation," Nature (2003) 421:384-388.

Wilens, T.E. et al., "A pilot controlled clinical trial of ABT-418, a cholinergic agonist, in the treatment of adults with attention deficit hyperactivity disorder," Am. J. Psych. (1999) 156(12):1931-1937.
Wolff, M.E., Burger's Medicinal Chemistry and Drug Discovery, 5th Edition, Part I, John Wiley & Sons (1995) 975-977.
Yasuda, T. et al., "Synthesis, solid structure, and optical properties of new thiophene-based alternating π-conjugated copolymers containing 4-alkyl-1,2,4-triazole or 1,3,4-thiadiazole unit as the partner unit," Macromolecules (2005) 38:1500-1503.
Zubets, I.V. et al., "Synthesis and mass-spectrometric study of 2-amino- and 2-chloro-5-aryl-1,3,4-thiadiazoles," Khimiya Geterotsiklicheskikh Soedinenii (1986) 10:1416-1419.
International Search Report and Written Opinion for Application No. PCT/US2007/083687 dated May 26, 2008 (12 pages).
International Preliminary Report on Patentability for Application No. PCT/US2007/083687 dated May 12, 2009 (8 pages).
International Search Report for Application No. PCT/US2011/052668 dated Oct. 26, 2011 (3 pages).
United States Patent Office Action for U.S. Appl. No. 11/935,157 dated Oct. 25, 2011 (6 pages).
United States Patent Office Action for U.S. Appl. No. 11/935,157 dated Mar. 14, 2011 (10 pages).
Shekunov, B.Y. et al., "Crystallization processes in pharmaceutical technology and drug delivery design," J. Crystal Growth (2000) 211(1-4):122-136.
Wishka D.G., et al., "Discovery of N-[(3R)-1-Azabicyclo[2.2.2]oct-3-yl]furo[2,3-c]pyridine-5-carboxamide, an Agonist of the α7 Nicotinic Acetylcholine Receptor, for the Potential Treatment of Cognitive Deficits in Schizophrenia: Synthesis and Structure—Activity Relationship," Journal of Medicinal Chemistry, 2006, vol. 49 (14), pp. 4425-4436.
Notice of Opposition mailed Jan. 16, 2015 for Costa Rica Application No. CR20140277 filed Jun. 13, 2014.
Non-Final Office Action mailed May 22, 2015 for U.S. Appl. No. 14/624,517, filed Feb. 17, 2015.
European Patent Office Action for Application No. 11764428.6 dated Jun. 25, 2015 (4 pages).
Berge, S.M. et al., "Pharmaceutical salts," J. Pharm. Sci. (1977) 6691):1-19.
Kitamura, M., "Development of controlling technology for polymorphic crystallization," J. of Japanese Association for Crystal Growth (2003) 30(3):19-20.
Ooshima, H., "Crystallization of polymorphs and pseudo-polymorphs and its control," Pharm. Stage (2007) 6(10):48-53.
Takata, N., "API form screening and selection in drug discovery stage," Pharm. Stage (2007) 6(10):20-25.
"Impurities: Guidelines for Residual Solvents Q3C(R5)," (Regarding guideline of residual solvent in medicaments), Notice No. 307 from the Evaluation and Licensing Division of the Pharmaceutical and Good Safety Bureau of the Ministry of Health, Labour and Welfare (1998) 29 pages.
"Specifications: test procedures and acceptance criteria for new drug substances and new drug products. Chemical substances" ICH Harmonised Tripartite Guideline (Setting the standard and test method for novel medicaments), Notice No. 568 from the Evaluation and Licensing Division in the Pharmaceutical and Good Safety Bureau of the Ministry of Health, Labour and Welfare (2001) 36 pages.
U.S. Patent Office Action for U.S. Appl. No. 14/624,517 dated Nov. 20, 2015 (8 pages).
Bauer, J.F. "Drying pharmaceutical solids—hydrates and enantiotropic polymorphs," J. Valid. Tech. (2009) 49-56.
Cavillari, C. et al., "Thermal study of anhydrous and hydrated forms of olanzapine," Pharm. Anal. Acta (2013) 4/5:7 pages.
Desiraju, G., "Cryptic crystallography," Nat. Mat. (2002) 1:77-79.
Savjani, K.T. et al., "Drug solubility: importance and enhancement techniques" International Scholarly Research Network (2012) Art ID No. 195727, 10 pages.
*Leo Pharma A/S et al.* vs. *Sandoz Limited*, Judgment in the High Court of Justice Chancery Division Patents Court, Case No. HC08C00391 dated May 15, 2009.
European Patent Office Action for application No. 11764428.6 dated Nov. 19, 2015 (5 pages).

* cited by examiner

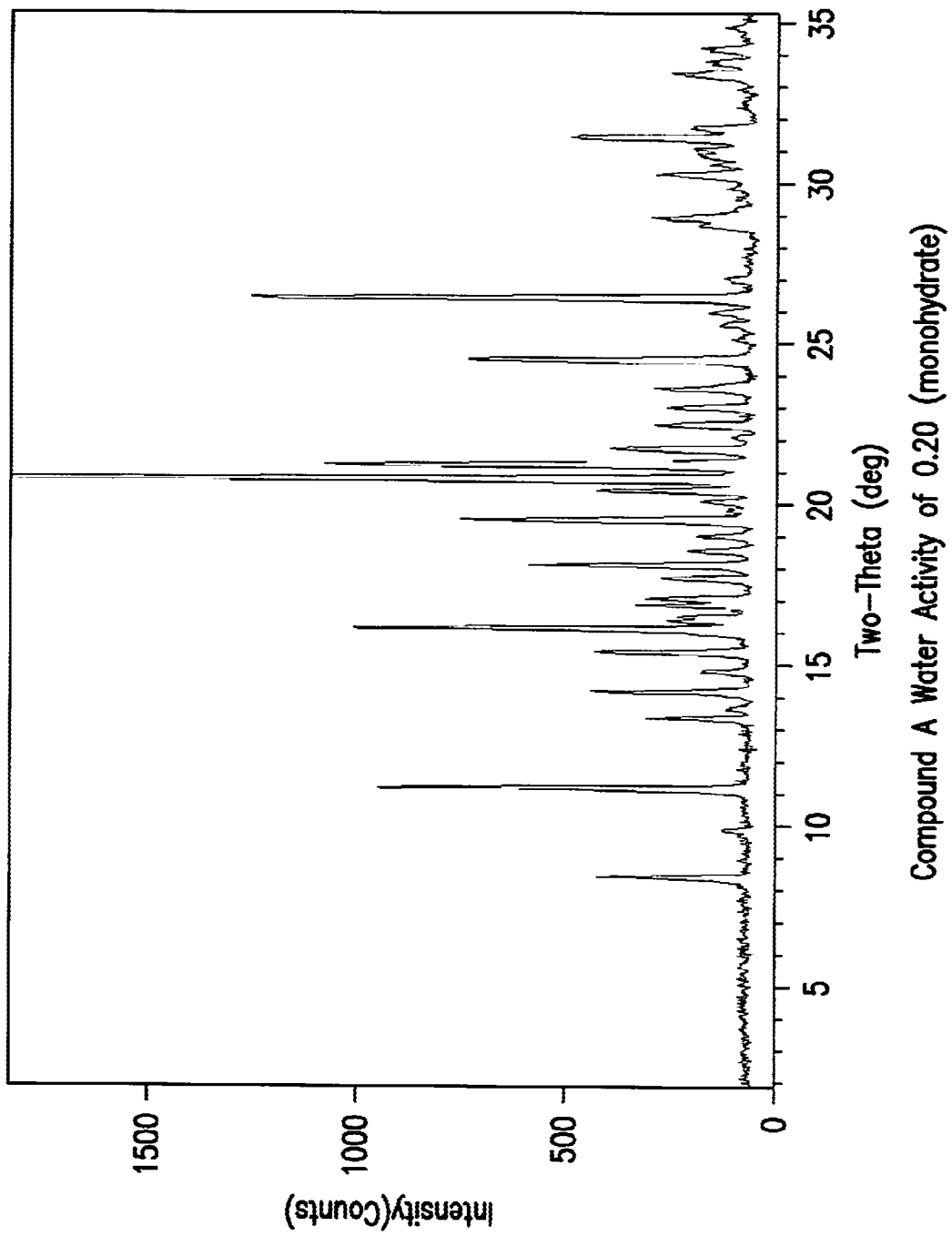

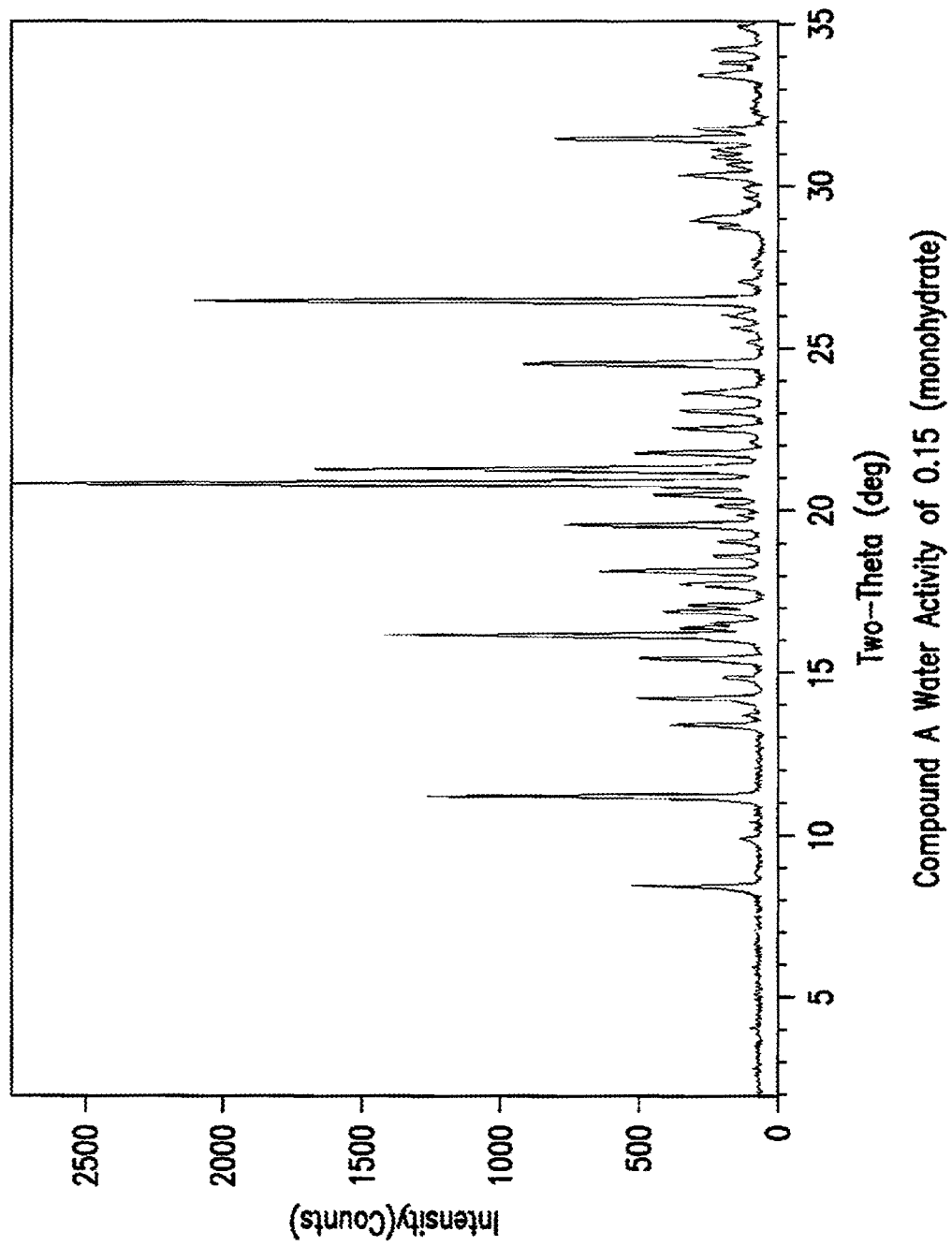

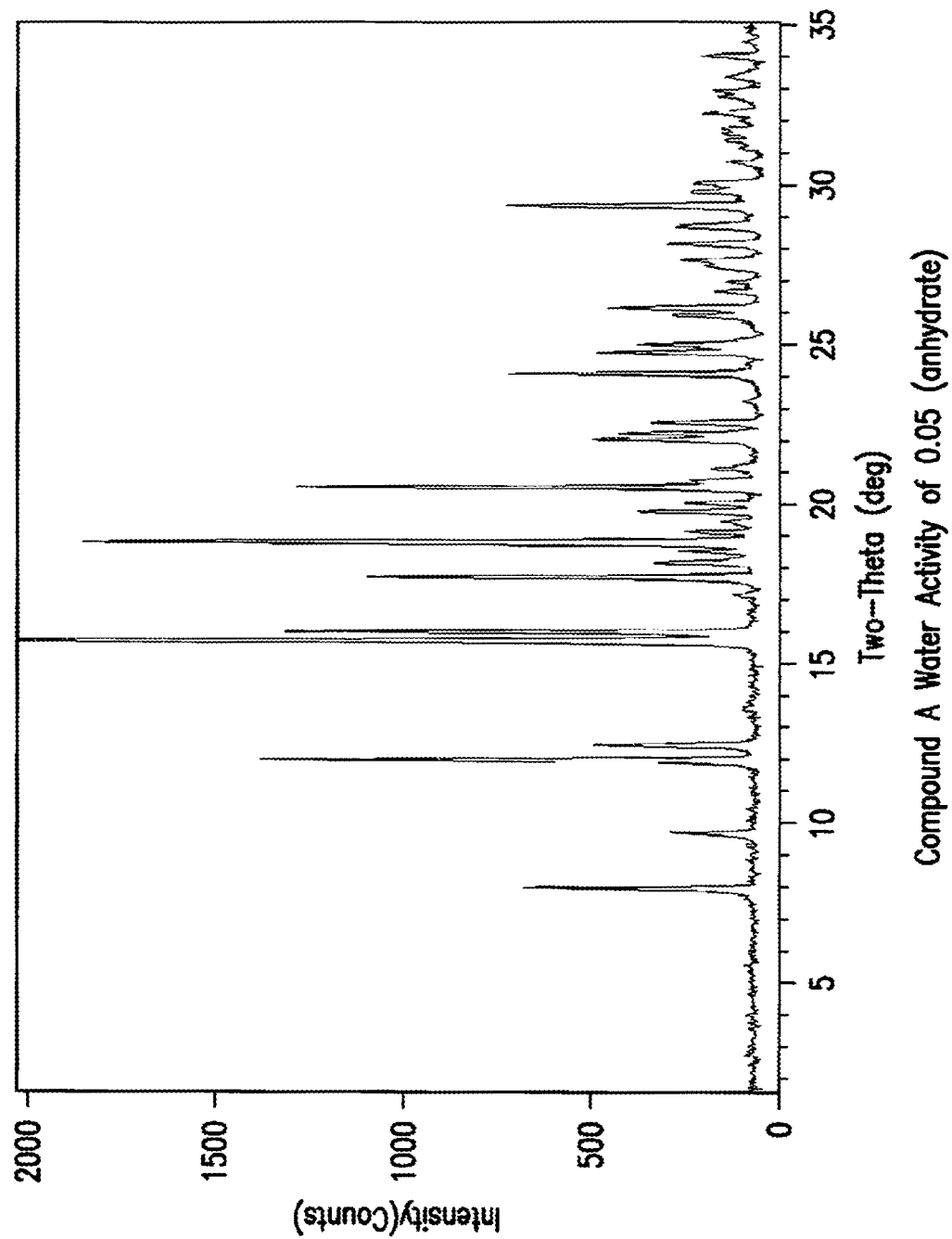

MONOHYDRATE OF AZAADAMANTANE DERIVATIVES

CROSS-REFERENCE TO RELATED APPLICATIONS

This application claims the benefit of U.S. Provisional Patent Application Ser. No. 61/385,674, filed on Sep. 23, 2010, which is herein incorporated by reference in its entirety.

STATEMENT REGARDING FEDERALLY SPONSORED RESEARCH OR DEVELOPMENT

Not applicable.

BACKGROUND OF THE INVENTION

1. Technical Field

The invention relates to azaadamantane derivatives, and more particularly, crystalline monohydrate forms of azaadamantane derivatives, compositions comprising such compounds, methods of preventing or treating conditions and disorders using such compounds and compositions, and processes for preparing such compounds.

2. Description of Related Technology

Nicotinic acetylcholine receptors (nAChRs) are widely distributed throughout the central (CNS) and peripheral (PNS) nervous systems. Such receptors play an important role in regulating CNS function, particularly by modulating release of a wide range of neurotransmitters, including, but not necessarily limited to, acetylcholine, norepinephrine, dopamine, serotonin, and GABA. Consequently, nicotinic receptors mediate a very wide range of physiological effects, and have been targeted for therapeutic treatment of disorders relating to cognitive function, learning and memory, neuro-degeneration, pain, inflammation, psychosis, sensory gating, mood, and emotion, among other conditions.

Many subtypes of the nAChR exist in the CNS and periphery. Each subtype has a different effect on regulating the overall physiological function. Typically, nAChRs are ion channels that are constructed from a pentameric assembly of subunit proteins. At least 12 subunit proteins, $\alpha 2$-$\alpha 10$ and $\beta 2$-$\beta 4$, have been identified in neuronal tissue. These subunits provide for a great variety of homomeric and heteromeric combinations that account for the diverse receptor subtypes. For example, the predominant receptor that is responsible for high affinity binding of nicotine in brain tissue has composition $(\alpha 4)_2(\beta 2)_3$ (the $\alpha 4\beta 2$ subtype), while another major population of receptors is comprised of homomeric $(\alpha 7)_5$ (the $\alpha 7$ subtype) receptors.

Certain compounds, like the plant alkaloid nicotine, interact with all subtypes of the nAChRs, accounting for the profound physiological effects of this compound. While nicotine has been demonstrated to have many beneficial properties, not all of the effects mediated by nicotine are desirable. For example, nicotine exerts gastrointestinal and cardiovascular side effects that interfere at therapeutic doses, and its addictive nature and acute toxicity are well-known. Ligands that are selective for interaction with only certain subtypes of the nAChR offer potential for achieving beneficial therapeutic effects with an improved margin for safety.

The $\alpha 7$ and $\alpha 4\beta 2$ nAChRs have been shown to play a significant role in enhancing cognitive function, including aspects of learning, memory and attention (Levin, E. D., J. Neurobiol. 53: 633-640, 2002). For example, $\alpha 7$ nAChRs have been linked to conditions and disorders related to attention deficit disorder, attention deficit hyperactivity disorder (ADHD), schizophrenia, Alzheimer's disease (AD), mild cognitive impairment, senile dementia, dementia associated with Lewy bodies, dementia associated with Down's syndrome, AIDS dementia, and Pick's disease, as well as inflammation. The $\alpha 4\beta 2$ receptor subtype is implicated in attention, cognition, epilepsy, and pain control (Paterson and Norberg, *Progress in Neurobiology* 61 75-111, 2000) as well as smoking cessation or nicotine withdrawal syndrome.

The activity at both $\alpha 7$ and $\alpha 4\beta 2$ nAChRs can be modified or regulated by the administration of subtype selective nAChR ligands. The ligands can exhibit antagonist, agonist, or partial agonist properties. Compounds that function as allosteric modulators are also known.

Although compounds that nonselectively demonstrate activity at a range of nicotinic receptor subtypes including the $\alpha 4\beta 2$ and $\alpha 7$ nAChRs are known, it would be beneficial to provide compounds that interact selectively with $\alpha 7$-containing neuronal nAChRs, $\alpha 4\beta 2$ nAChRs, or both $\alpha 7$ and $\alpha 4\beta 2$ nAChRs compared to other subtypes.

In view of this need within the art, the inventors were involved with others, and developed the novel azaadamantane derivatives disclosed in co-pending publications. Specifically, U.S. Patent Application Publication No. 2008/0167336 (hereinafter referred to as the "'336 publication") was directed to azaadamantane derivatives and the salt forms of the compound. The '336 publication indicates that the certain compounds disclosed therein may exist as salts of the compound of the invention. The salts of such compound include, but are not limited to, L-bitartrate anhydrate, L-bitartrate hydrate, dihydrogen phosphate anhydrate, dihydrogen phosphate hydrate, bisuccinate anhydrate, bisuccinate hydrate, hydrochloride quarterhydrate, hydrochloride sesquihydrate, dihydrogen citrate, and monohydrogen citrate. These compounds are considered important due to their selective interaction with $\alpha 7$-containing neuronal nAChRs, $\alpha 4\beta 2$ nAChRs, or both $\alpha 7$ and $\alpha 4\beta 2$ nAChRs compared to other compounds known in the art.

BRIEF DESCRIPTION OF THE DRAWINGS

FIG. 4(b) illustrates the X-ray powder diffraction pattern for a (4s)-4-(5-phenyl-1,3,4-thiadiazol-2-yloxy)-1-azatricyclo[3.3.1.1$^{3,7}$]decane dihydrogen citrate (Compound A) solid recovered from a suspension having a water activity of 0.20.

FIG. 4(c) illustrates the X-ray powder diffraction pattern for a (4s)-4-(5-phenyl-1,3,4-thiadiazol-2-yloxy)-1-azatricyclo[3.3.1.1$^{3,7}$]decane dihydrogen citrate (Compound A) solid recovered from a suspension having a water activity of 0.15.

FIG. 4(e) illustrates the X-ray powder diffraction pattern for a (4s)-4-(5-phenyl-1,3,4-thiadiazol-2-yloxy)-1-azatricyclo[3.3.1.1$^{3,7}$]decane dihydrogen citrate (Compound A) solid recovered from a suspension having a water activity of 0.05.

SUMMARY OF THE INVENTION

Figure 1:
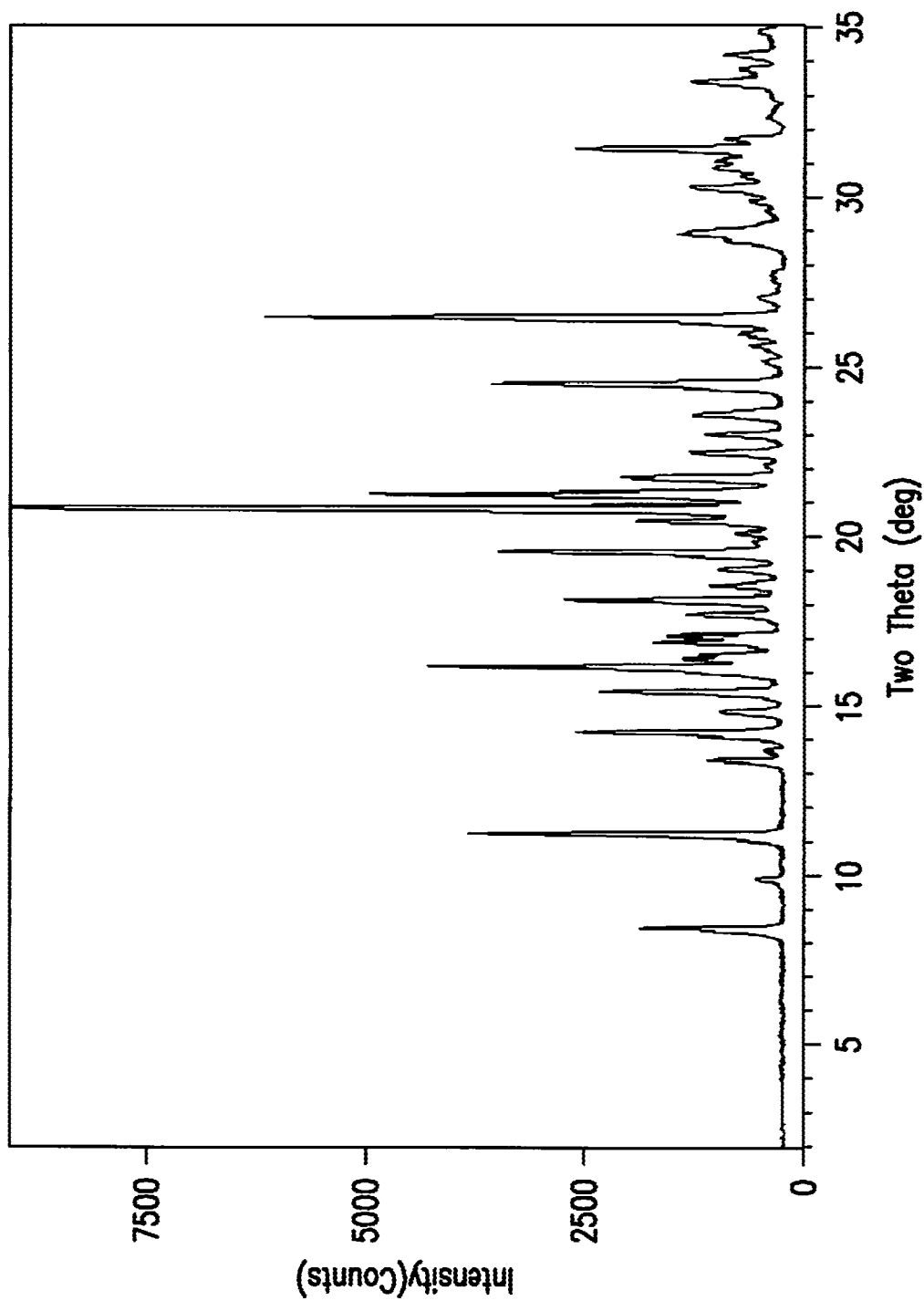
FIG. 1 is a powder X-ray diffraction pattern of a crystalline monohydrate salt of (4s)-4-(5-phenyl-1,3,4-thiadiazol-2-yloxy)-1-azatricyclo[3.3.1.1$^{3,7}$]decane dihydrogen citrate.

The compounds of the '336 publication were subjected to a thorough salt screening to determine primary compounds of interest. In the process of testing the salt compositions, the dihydrogen citrate anhydrate salt of (4s)-4-(5-phenyl-1,3,4-thiadiazol-2-yloxy)-1-azatricyclo[3.3.1.1$^{3,7}$]decane was identified as a compound of particular interest due to favorable solid state properties, pharmaceutical properties, and manufacturing properties. In view of these favorable characteristics, (4s)-4-(5-phenyl-1,3,4-thiadiazol-2-yloxy)-1-azatricyclo[3.3.1.1$^{3,7}$]decane dihydrogen citrate was selected for additional analysis, including polymorph screening and polymorph analysis. Accordingly, the current invention is directed to the crystalline monohydrate salt of (4s)-4-(5-phenyl-1,3,4-thiadiazol-2-yloxy)-1-azatricyclo[3.3.1.1$^{3,7}$]decane dihydrogen citrate and related methods and processes thereof.

One embodiment of the invention relates to the crystalline salt of (4s)-4-(5-phenyl-1,3,4-thiadiazol-2-yloxy)-1-azatricyclo[3.3.1.1$^{3,7}$]decane having formula (I)

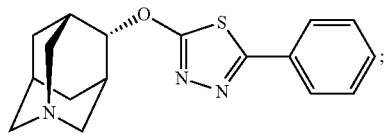

(I)

wherein the salt comprises dihydrogen citrate having formula (II)

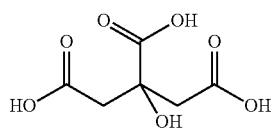

(II)

In an additional embodiment, the crystalline monohydrate salt of (4s)-4-(5-phenyl-1,3,4-thiadiazol-2-yloxy)-1-azatricyclo[3.3.1.1$^{3,7}$]decane dihydrogen citrate has a purity of at least 90% of the monohydrate form and not greater than 10% of the non-monohydrate form. In yet an additional embodiment, the crystalline monohydrate salt of (4s)-4-(5-phenyl-1,3,4-thiadiazol-2-yloxy)-1-azatricyclo[3.3.1.1$^{3,7}$]decane dihydrogen citrate has a purity of at least 95% of the monohydrate form and not greater than 5% of the non-monohydrate form. In still yet a further additional embodiment, the crystalline monohydrate salt of (4s)-4-(5-phenyl-1,3,4-thiadiazol-2-yloxy)-1-azatricyclo[3.3.1.1$^{3,7}$]decane dihydrogen citrate has a purity of at least 97% and not greater than 3% of the non-monohydrate form.

In a further embodiment, the crystalline monohydrate of (4s)-4-(5-phenyl-1,3,4-thiadiazol-2-yloxy)-1-azatricyclo [3.3.1.1$^{3,7}$]decane dihydrogen citrate demonstrates at least one characteristic peak in the powder X-ray diffraction pattern at values in degrees two theta of 8.4±0.20, 11.3±0.20, 14.2±0.20, 15.5±0.20, 16.4±0.20, 16.6±0.20, 17.2±0.20, 19.7±0.20, 20.7±0.20, 21.0±0.20, 21.2±0.20, 21.6±0.20, 24.8±0.20, and 26.9±0.20.

In yet another embodiment, the crystalline monohydrate of (4s)-4-(5-phenyl-1,3,4-thiadiazol-2-yloxy)-1-azatricyclo [3.3.1.1$^{3,7}$]decane dihydrogen citrate of claim 1, has unit cell parameters wherein a is about 6.52 Å, b is about 20.99 Å, c is about 16.83 Å, α is about 90.0°, β is about 93.75°, γ is about 90.0°, the volume is about 2297.52 Å$^3$, and Z is about 4.

In another embodiment, the crystalline monohydrate of (4s)-4-(5-phenyl-1,3,4-thiadiazol-2-yloxy)-1-azatricyclo [3.3.1.1$^{3,7}$]decane dihydrogen citrate exhibits non-hygroscopic qualities when evaluated by dynamic moisture sorption gravimetry, having a weight loss of less than approximately 0.2% from relative humidities of 0% to 90%.

Another embodiment of the invention relates to pharmaceutical compositions comprising compounds of the invention. Such compositions can be administered in accordance with a methods of the invention, typically as part of a therapeutic regimen for treatment or prevention of conditions and disorders related to nAChR activity, and more particularly α7 nAChR activity, α4β2 nAChR activity, or both α7 nAChR activity and α4β2 nAChR activity.

Yet another embodiment of the invention relates to a method of modulating both α7 and α4β2 nAChR activity. The method is useful for treating, preventing or both treating and preventing conditions and disorders related to both α7 and α4β2 nAChR activity, particularly in mammals.

A further embodiment of the invention relates to a method of selectively modulating nAChR activity, for example α7 nAChR activity. The method is useful for treating, preventing or both treating and preventing conditions and disorders related to α7 nAChR activity in mammals. A method of selectively modulating α4β2 nAChR activity also is contemplated.

Such methods are useful for conditions and disorders related to attention deficit disorder, attention deficit hyperactivity disorder (ADHD), Alzheimer's disease (AD), schizophrenia, mild cognitive impairment, age-associated memory impairment (AAMI), senile dementia, AIDS dementia, Pick's disease, dementia associated with Lewy bodies, dementia associated with Down's syndrome, schizophrenia, smoking cessation, nicotinic withdrawal syndrome, amyotrophic lateral sclerosis, Huntington's disease, diminished CNS function associated with traumatic brain injury, acute pain, post-surgical pain, chronic pain, inflammatory pain, neuropathic pain, infertility, lack of circulation, need for new blood vessel growth associated with wound healing, more particularly circulation around a vascular occlusion, need for new blood vessel growth associated with vascularization of skin grafts, ischemia, inflammation, sepsis, wound healing, and other complications associated with diabetes, among other systemic and neuroimmunomodulatory activities.

An additional embodiment of the invention relates to a method for producing the crystalline monohydrate salt of the current invention, using a dihydrogen citrate anhydrate salt as the starting material. Specifically, the process for preparing a crystalline monohydrate salt of (4s)-4-(5-phenyl-1,3,4-thiadiazol-2-yloxy)-1-azatricyclo[3.3.1.1$^{3,7}$]decane dihydrogen citrate the process comprises the steps of: (a) dissolving (4s)-4-(5-phenyl-1,3,4-thiadiazol-2-yloxy)-1-azatricyclo[3.3.1.1$^{3,7}$]decane in at least one solvent at a temperature ranging from approximately 65° C. to approximately 85° C.; (b) adjusting the temperature of the solution to a temperature ranging from approximately 55° C. to approximately 75° C. over a period of at least thirty minutes; (c) adding at least one additional solvent to the solution and mixing for a period of at least thirty minutes; (d) adjusting the temperature of the solutions to a temperature ranging from approximately 30° C. to approximately 50° C. over a period greater than two hours; (e) adding at least one additional solvent to the solution over a period of not less than three hours; (0 maintaining the slurry at a temperature ranging from approximately 30° C. to approximately 50° C. for a period of at least one hour; (g) adjusting the temperature of the slurry to a temperature ranging from approximately −5° C. to approximately 15° C.; (h) mixing the slurry for at least one hour; and (i) recovering the crystalline monohydrate salt of (4s)-4-(5-phenyl-1,3,4-thiadiazol-2-yloxy)-1-azatricyclo[3.3.1.1$^{3,7}$]decane dihydrogen citrate.

The solvent of step (a) may comprise an organic solvent, water, and combinations thereof. In a further embodiment, the solvent of step (a) is selected from the group consisting of methanol, ethanol, 2-propanol, butanol, butanol acetonitrile, acetone, formamide, dimethyl formamide, toluene, benzene, anisole, ethyl acetate, isopropyl acetate, tetrahydrofuran, 1,4-dioxane, methyl tert-butyl ether, dichloromethane, chloroform, hexanes, n-heptane, 2-butanone, dimethyl sulfoxide, nitromethane, 1-methyl-2-pyrrolidone, triethylamine, tributylamine, trifluorotoluene, water, and mixtures thereof. In a preferred embodiment, the solvent of step (a) comprises a mixture of 2-propanol and water. The mixture of 2-propanol and water may comprise a ratio of 2-propanol to water ranging from approximately 1:10 to approximately 10:1. In a more preferred embodiment, the mixture of 2-propanol and water may comprise a ratio of 2-propanol to water ranging from approximately 3:1 to approximately 5:1. Additionally, the temperature of step (a) may range from approximately 70° C. to approximately 80° C., and, in a more preferred embodiment, the temperature of step (a) may range from approximately 74° C. to approximately 76° C.

Step (b) may comprise adjusting the temperature of the solution to a temperature of approximately 60° C. to approximately 70° C. over a period of at least thirty minutes. In a preferred iteration, step (b) may comprise adjusting the temperature of the solution to a temperature of approximately 64° C. to approximately 66° C. over a period of at least thirty minutes.

The solvent of step (c) may comprise an organic solvent, water, and combinations thereof. In a preferred embodiment, the solvent of step (c) may be selected from the group consisting of methanol, ethanol, 2-propanol, butanol, butanol acetonitrile, acetone, formamide, dimethyl formamide, toluene, benzene, anisole, ethyl acetate, isopropyl acetate, tetrahydrofuran, 1,4-dioxane, methyl tert-butyl ether, dichloromethane, chloroform, hexanes, n-heptane, 2-butanone, dimethyl sulfoxide, nitromethane, 1-methyl-2-pyrrolidone, triethylamine, tributylamine, trifluorotoluene, water, and mixtures thereof. In a more preferred embodiment, the solvent of step (c) may comprise 2-propanol. Additionally, the amount of 2-propanol used in step (c) may comprise approximately 2 volumes to approximately 10 volumes, relative to the amount of solvent incorporated in step (a). In a preferred embodiment, the amount of 2-propanol used in step (c) may comprise approximately 5 volumes to approximately 7 volumes compared to the amount of solvent used in step (a).

Step (d) may comprise adjusting the temperature to approximately 35° C. to approximately 45° C. over a period greater than two hours. In a preferred iteration of the method, step (d) may comprise adjusting the temperature to approximately 39° C. to approximately 41° C. over a period of time ranging from approximately 30 minutes to approximately eight hours. However, one skilled in the art will appreciate that the time may be expanded without departing from the scope of the invention.

The solvent of step (e) may comprise an organic solvent, water, and combinations thereof. In an preferred embodiment, the solvent of step (e) may be selected from the group consisting of methanol, ethanol, 2-propanol, butanol, butanol acetonitrile, acetone, formamide, dimethyl formamide, toluene, benzene, anisole, ethyl acetate, isopropyl acetate, tetrahydrofuran, 1,4-dioxane, methyl tert-butyl ether, dichloromethane, chloroform, hexanes, n-heptane, 2-butanone, dimethyl sulfoxide, nitromethane, 1-methyl-2-pyrrolidone, triethylamine, tributylamine, trifluorotoluene, water, and mixtures thereof. In a more preferred embodiment, the solvent of step (e) may comprise 2-propanol. Additionally, the amount of 2-propanol used in step (e) may comprise approximately 1 volume to approximately 10 volumes, relative to the amount of solvent incorporated in step (a). In a preferred embodiment, the amount of 2-propanol used in step (e) may comprise approximately 4 volumes to approximately 6 volumes compared to the amount of solvent used in step (a).

Step (f) may comprise adjusting the temperature of the reaction to approximately 35° C. to approximately 45° C. for a period of at least one hour. In a preferred embodiment, step (f) may comprise adjusting the temperature to approximately 39° C. to approximately 41° C. for a period of at least one hour.

Step (g) may comprise adjusting the temperature of the slurry to a temperature ranging from approximately 0° C. to approximately 10° C. In a more preferred embodiment, step (g) may comprise adjusting the temperature of the slurry to a temperature ranging from approximately 4° C. to approximately 6° C.

Further, step (i) may comprise recovering the crystalline monohydrate salt of (4s)-4-(5-phenyl-1,3,4-thiadiazol-2-yloxy)-1-azatricyclo[3.3.1.1$^{3,7}$]decane dihydrogen citrate by filtration.

In another embodiment, the current invention comprises a process for preparing a crystalline monohydrate salt of (4s)-4-(5-phenyl-1,3,4-thiadiazol-2-yloxy)-1-azatricyclo[3.3.1.1$^{3,7}$]decane dihydrogen citrate the process comprising the steps of: (a) dissolving (4s)-4-(5-phenyl-1,3,4-thiadiazol-2-yloxy)-1-azatricyclo[3.3.1.1$^{3,7}$]decane in approximately 4 volumes of 2-propanol and approximately 1 volume of water at a temperature of approximately 75° C.; (b) adjusting the temperature of the solution to a temperature ranging from approximately 65° C. over a period of at least thirty minutes; (c) adding approximately 6 volumes of 2-propanol to the solution and mixing for a period of at least thirty minutes; (d) adjusting the temperature to approximately 40° C. over a period greater than two hours; (e) adding approximately 5 volumes of 2-propanol to the solution over a period of not less than three hours; (f) maintaining the slurry at a temperature of approximately 40° C. for a period of at least one hour; (g) adjusting the temperature of the slurry to a temperature of approximately 5° C.; (h) mixing the slurry for at least one hour; and (i) recovering the crystalline monohydrate salt of (4s)-4-(5-phenyl-1,3,4-thiadiazol-2-yloxy)-1-azatricyclo[3.3.1.1$^{3,7}$]decane.

In an alternative embodiment, the current invention also comprises a process for preparing a crystalline monohydrate salt of (4s)-4-(5-phenyl-1,3,4-thiadiazol-2-yloxy)-1-azatricyclo[3.3.1.1$^{3,7}$]decane dihydrogen citrate, the process comprising the steps of: (a) contacting anhydrous (4s)-4-(5-phenyl-1,3,4-thiadiazol-2-yloxy)-1-azatricyclo[3.3.1.1$^{3,7}$] decane dihydrogen citrate with a solvent in a reaction vessel; (b) sealing the reaction vessel and protecting the suspension from light at ambient conditions; and; and (c) recovering the crystalline monohydrate salt of (4s)-4-(5-phenyl-1,3,4-thiadiazol-2-yloxy)-1-azatricyclo[3.3.1.1$^{3,7}$]decane.

According to this method, the solvent of step (a) may comprise water. Additionally, the amount of anhydrous (4s)-4-(5-phenyl-1,3,4-thiadiazol-2-yloxy)-1-azatricyclo [3.3.1.1$^{3,7}$]decane dihydrogen citrate may comprise approximately 100 mg to approximately 300 mg, and the amount of water may comprise approximately 0.1 mL to approximately 2.0 mL. In a further preferred embodiment, the amount of anhydrous (4s)-4-(5-phenyl-1,3,4-thiadiazol-2-yloxy)-1-azatricyclo[3.3.1.1$^{3,7}$]decane dihydrogen citrate comprises approximately 150 mg to approximately 250 mg, and wherein the amount of water comprises approximately 0.8 mL to approximately 1.2 mL. One skilled in the art will also appreciate that the solvent of step (a) may comprise a mixture of an organic solvent and water. Moreover, the organic solvent may comprise methanol, ethanol, 2-propanol, butanol, butanol acetonitrile, acetone, formamide, dimethyl formamide, toluene, benzene, anisole, ethyl acetate, isopropyl acetate, tetrahydrofuran, 1,4-dioxane, methyl tert-butyl ether, dichloromethane, chloroform, hexanes, n-heptane, 2-butanone, dimethyl sulfoxide, nitromethane, 1-methyl-2-pyrrolidone, triethylamine, tributylamine, trifluorotoluene, and mixtures thereof.

In a further alternative embodiment, the current invention comprises a pharmaceutical composition comprising the crystalline monohydrate salt of (4s)-4-(5-phenyl-1,3,4-thiadiazol-2-yloxy)-1-azatricyclo[3.3.1.1$^{3,7}$]decane dihydrogen citrate as an active ingredient and a pharmaceutically acceptable carrier, diluent, or excipient. In a preferred embodiment of the pharmaceutical composition, the crystalline monohydrate of (4s)-4-(5-phenyl-1,3,4-thiadiazol-2-yloxy)-1-azatricyclo[3.3.1.1$^{3,7}$]decane dihydrogen citrate is present in an amount ranging from approximately 0.1% to approximately 99.9% by weight based on the total weight of the composition. In this embodiment, the pharmaceutical composition comprising the crystalline monohydrate of (4s)-4-(5-phenyl-1,3,4-thiadiazol-2-yloxy)-1-azatricyclo[3.3.1.1$^{3,7}$]decane dihydrogen citrate demonstrates at least one characteristic peak in the powder X-ray diffraction pattern at values in degrees two theta of 8.4±0.20, 11.3±0.20, 14.2±0.20, 15.5±0.20, 16.4±0.20, 16.6±0.20, 17.2±0.20, 19.7±0.20, 20.7±0.20, 21.0±0.20, 21.2±0.20, 21.6±0.20, 24.8±0.20, and 26.9±0.20.

DETAILED DESCRIPTION OF THE INVENTION

The compound (4s)-4-(5-phenyl-1,3,4-thiadiazol-2-yloxy)-1-azatricyclo[3.3.1.1$^{3,7}$]decane is known to exist in multiple salt forms, as reported in the co-pending '336 publication. One of the salt forms, the dihydrogen citrate salt, was identified as a primary compound of interest, due to several observed benefits associated with the compound. Specifically, the dihydrogen citrate anhydrate exhibited favorable solid state properties including high crystallinity, acceptable melting point, non-hygroscopicity, and the ability to avoid exhibiting complex polymorphisms. In addition, the dihydrogen citrate anhydrate salt showed beneficial pharmaceutical properties, including a solid state stability in the form of stability at 40° C. and 75% relative humidity for 12 weeks, stability when exposed to a UV/Visible ICH Type I light source, and stability when exposed to peroxide vapor at 40° C. for eight days. The dihydrogen citrate anhydrate also showed a solubility of 28 mg/mL in water. Furthermore, the dihydrogen citrate anhydrate also demonstrates beneficial manufacturing properties, such that the compound can be manufactured with acceptable purity and yield, and the particle size can be controlled by milling.

In view of these favorable characteristics, (4s)-4-(5-phenyl-1,3,4-thiadiazol-2-yloxy)-1-azatricyclo[3.3.1.1$^{3,7}$]decane dihydrogen citrate was selected for additional analysis, including polymorph screening and polymorph analysis. It was noted that (4s)-4-(5-phenyl-1,3,4-thiadiazol-2-yloxy)-1-azatricyclo[3.3.1.1$^{3,7}$]decane dihydrogen citrate, when prepared according to the methods of the '336 publication, was recovered as an anhydrate. As such, the inventors of the current invention subjected the dihydrogen citrate anhydrate to polymorph screening and thermodynamic analysis to determine if other forms of the compound could be produced. Specifically, the dihydrogen citrate was suspended in a variety of solvents to determine if other crystal forms could be produced.

The novel monohydrate of the current invention exhibits beneficial properties when compared to the compounds disclosed in the '336 publication. Specifically, the monohydrate of the present invention is a thermodynamically stable form of the salt under conditions of higher water activity, higher relative humidity, or higher water activity and higher relative humidity, such that the monohydrate provides better chemical and physical stability when exposed to higher humidity and higher water activity environments, compared to the anhydrate. These types of conditions may be prevalent in certain types of pharmaceutical compositions such as solutions, suspensions, or any parenteral formulations. The dihydrogen citrate monohydrate form of the current invention also offers benefits in formulation processing. The process of wet granulation is commonly used for the preparation of pharmaceutical active ingredients. During wet granulation, the use of the monohydrate form could avoid any conversion from the anhydrate to the monohydrate, resulting in stability issues. Accordingly, the dihydrogen citrate monohydrate provides physical and chemical stability properties that were previously unavailable.

The dihydrogen citrate monohydrate compounds of the current invention generally incorporate one molecule of (4s)-4-(5-phenyl-1,3,4-thiadiazol-2-yloxy)-1-azatricyclo [3.3.1.1$^{3,7}$]decane, having chemical formula (I), and one molecule of the salt of citric acid (i.e., dihydrogen citrate) having chemical formula (II). Although the current invention is primarily focused on the (4s)-diastereomer of the azaadamantane compound, the compounds of the current invention can exist in the forms represented by formula (Ia) and (Ib):

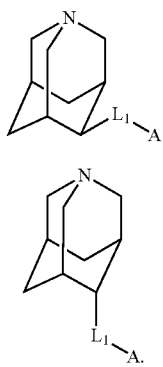

(Ia)

(Ib)

The aza-adamantane portion of isomer (Ia) and isomer (Ib) is not chiral, however the C-4 carbon at which $L_1$ is attached is considered pseudoasymmetric. Compounds represented by formula (Ia) and (Ib) are diastereomers. The configurational assignment of structures of formula (Ia) are assigned 4r in accordance with that described in Synthesis, 1992, 1080, Becker, D. P.; Flynn, D. L. and as defined in Stereochemistry of Organic Compounds, E. L. Eliel, S. H Wilen; John Wiley and Sons, Inc. 1994. In addition the configurational assignment of structures of formula (Ib) are assigned 4s using the same methods.

The isomers (Ia) and (Ib) may be synthesized separately using the individual steroisomers according to the schemes and the examples described herein. Alternatively, isomers (Ia) and (Ib) may be synthesized together after which the individual isomers may be separated by chromatographic methods from the mixture of both isomers when mixtures of stereoisomers are used in the synthesis. The mixtures of isomers may also be separated through fractional crystallization of salts of amines contained in the compounds of formula (I) made with enantiomerically pure carboxylic acids.

The current invention is directed to (4s)-4-(5-phenyl-1,3,4-thiadiazol-2-yloxy)-1-azatricyclo[3.3.1.1$^{3,7}$]decane dihydrogen citrate monohydrate crystalline solid, which can be identified by characteristic peaks in its powder X-ray diffraction pattern, as illustrated in FIG. 1. One with skill in the art of analytical chemistry would be able to readily identify (4s)-4-(5-phenyl-1,3,4-thiadiazol-2-yloxy)-1-azatricyclo[3.3.1.1$^{3,7}$]decane dihydrogen citrate monohydrate solid by as few as one characteristic peak in its powder X-ray diffraction pattern. Two-theta angle positions of characteristic peaks in a powder X-ray diffraction pattern of (4s)-4-(5-phenyl-1,3,4-thiadiazol-2-yloxy)-1-azatricyclo[3.3.1.1$^{3,7}$]decane dihydrogen citrate are 8.4±0.20, 11.3±0.20, 14.2±0.20, 15.5±0.20, 16.4±0.20, 16.6±0.20, 17.2±0.20, 19.7±0.20, 20.7±0.20, 21.0±0.20, 21.2±0.20, 21.6±0.20, 24.8±0.20, and 26.9±0.20. Thus, the crystalline (4s)-4-(5-phenyl-1,3,4-thiadiazol-2-yloxy)-1-azatricyclo[3.3.1.1$^{3,7}$]decane dihydrogen citrate monohydrate of the present invention demonstrates at least one characteristic peak in a powder X-ray diffraction pattern at values in degrees two theta of 8.4±0.20, 11.3±0.20, 14.2±0.20, 15.5±0.20, 16.4±0.20, 16.6±0.20, 17.2±0.20, 19.7±0.20, 20.7±0.20, 21.0±0.20, 21.2±0.20, 21.6±0.20, 24.8±0.20, and 26.9±0.20. Additionally, the present invention further contemplates that the crystalline (4s)-4-(5-phenyl-1,3,4-thiadiazol-2-yloxy)-1-azatricyclo[3.3.1.1$^{3,7}$]decane dihydrogen citrate monohydrate demonstrates at least two, at least three, at least four, at least five, at least six, at least seven, at least eight, at least nine, at least ten, at least eleven, at least twelve or at least thirteen characteristic peaks in a powder X-ray diffraction pattern at values in degrees two theta of 8.4±0.20, 11.3±0.20, 14.2±0.20, 15.5±0.20, 16.4±0.20, 16.6±0.20, 17.2±0.20, 19.7±0.20, 20.7±0.20, 21.0±0.20, 21.2±0.20, 21.6±0.20, 24.8±0.20, and 26.9±0.20. Moreover, the present invention further contemplates that the crystalline (4s)-4-(5-phenyl-1,3,4-thiadiazol-2-yloxy)-1-azatricyclo[3.3.1.1$^{3,7}$] decane dihydrogen citrate monohydrate demonstrates the following fourteen characteristic peaks in a powder X-ray diffraction pattern at values in degrees two theta of 8.4±0.20, 11.3±0.20, 14.2±0.20, 15.5±0.20, 16.4±0.20, 16.6±0.20, 17.2±0.20, 19.7±0.20, 20.7±0.20, 21.0±0.20, 21.2±0.20, 21.6±0.20, 24.8±0.20, and 26.9±0.20.

Figure 2:
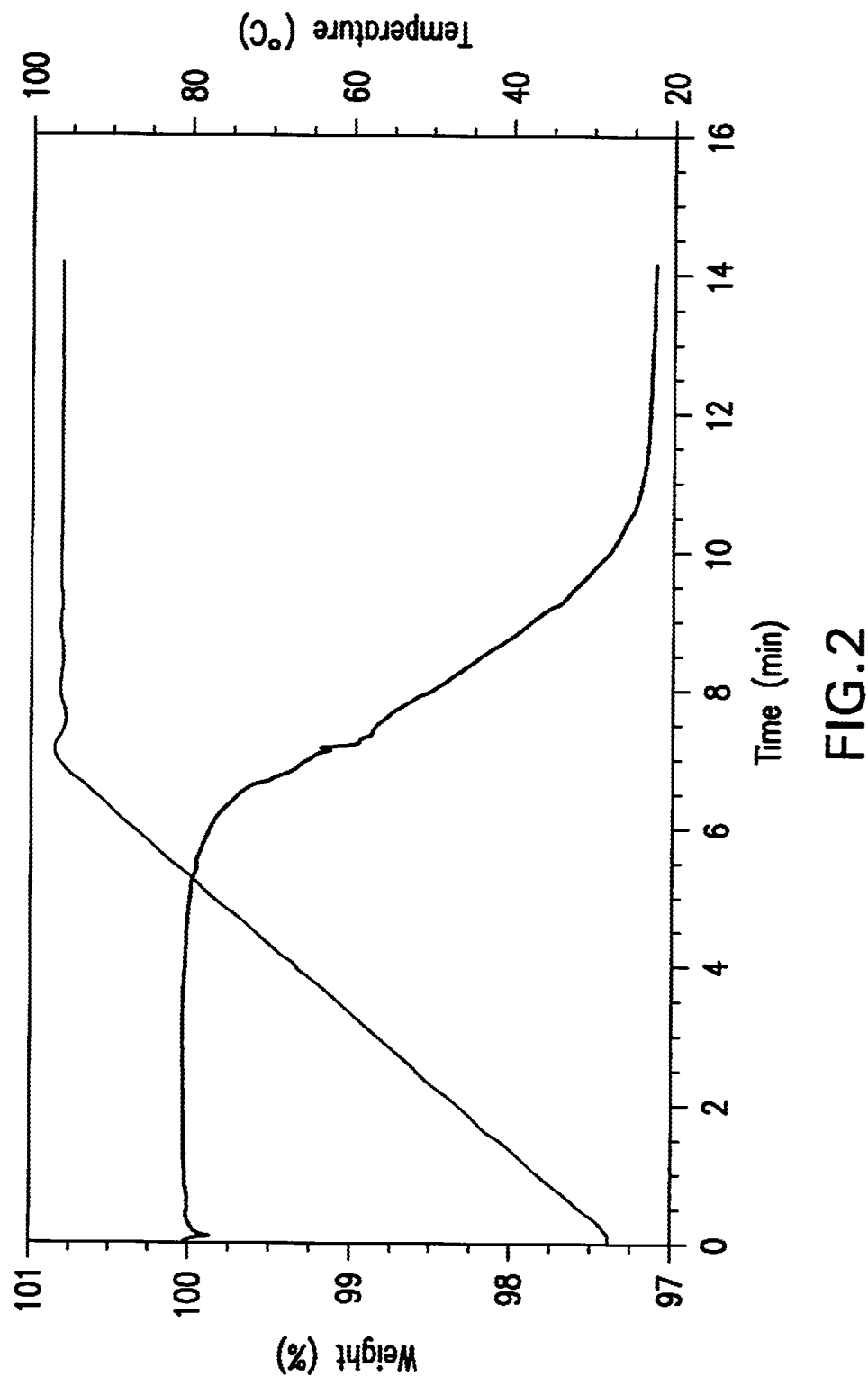
FIG. 2 is a thermogram of a crystalline salt of (4s)-4-(5-phenyl-1,3,4-thiadiazol-2-yloxy)-1-azatricyclo[3.3.1.1$^{3,7}$]decane dihydrogen citrate monohydrate.

Further, the thermogravimetric analysis (TGA) of (4s)-4-(5-phenyl-1,3,4-thiadiazol-2-yloxy)-1-azatricyclo[3.3.1.1$^{3,7}$]decane dihydrogen citrate monohydrate is illustrated in FIG. 2. The thermogravimetric analysis shows the dehydration of (4s)-4-(5-phenyl-1,3,4-thiadiazol-2-yloxy)-1-azatricyclo[3.3.1.1$^{3,7}$]decane dihydrogen citrate monohydrate as the temperature is increased. Specifically, the monohydrate salt illustrates a loss of mass of approximately 2.5% to approximately 3.5%, with an onset of approximately 60° C. to approximately 70° C. In a preferred embodiment, the monohydrate salt of (4s)-4-(5-phenyl-1,3,4-thiadiazol-2-yloxy)-1-azatricyclo[3.3.1.1$^{3,7}$]decane dihydrogen citrate illustrates a loss of mass of approximately 2.9%, with an onset at approximately 65° C.

The crystallographic unit cell parameters of (4s)-4-(5-phenyl-1,3,4-thiadiazol-2-yloxy)-1-azatricyclo[3.3.1.1$^{3,7}$]decane dihydrogen citrate monohydrate also were obtained and were determined according to the following parameters: a is 6.519 Å, b is 20.982 Å, c is 16.833 Å, α is about 90.0°, β is about 93.75°, and γ is about 90.0° to afford a cell volume of about 2297.52 Å$^3$, wherein a, b, and c are each a representative length of the crystal lattice and α, β, and γ are all unit cell angles. The salt crystallizes in the monoclinic P21/n space group.

Figure 3:
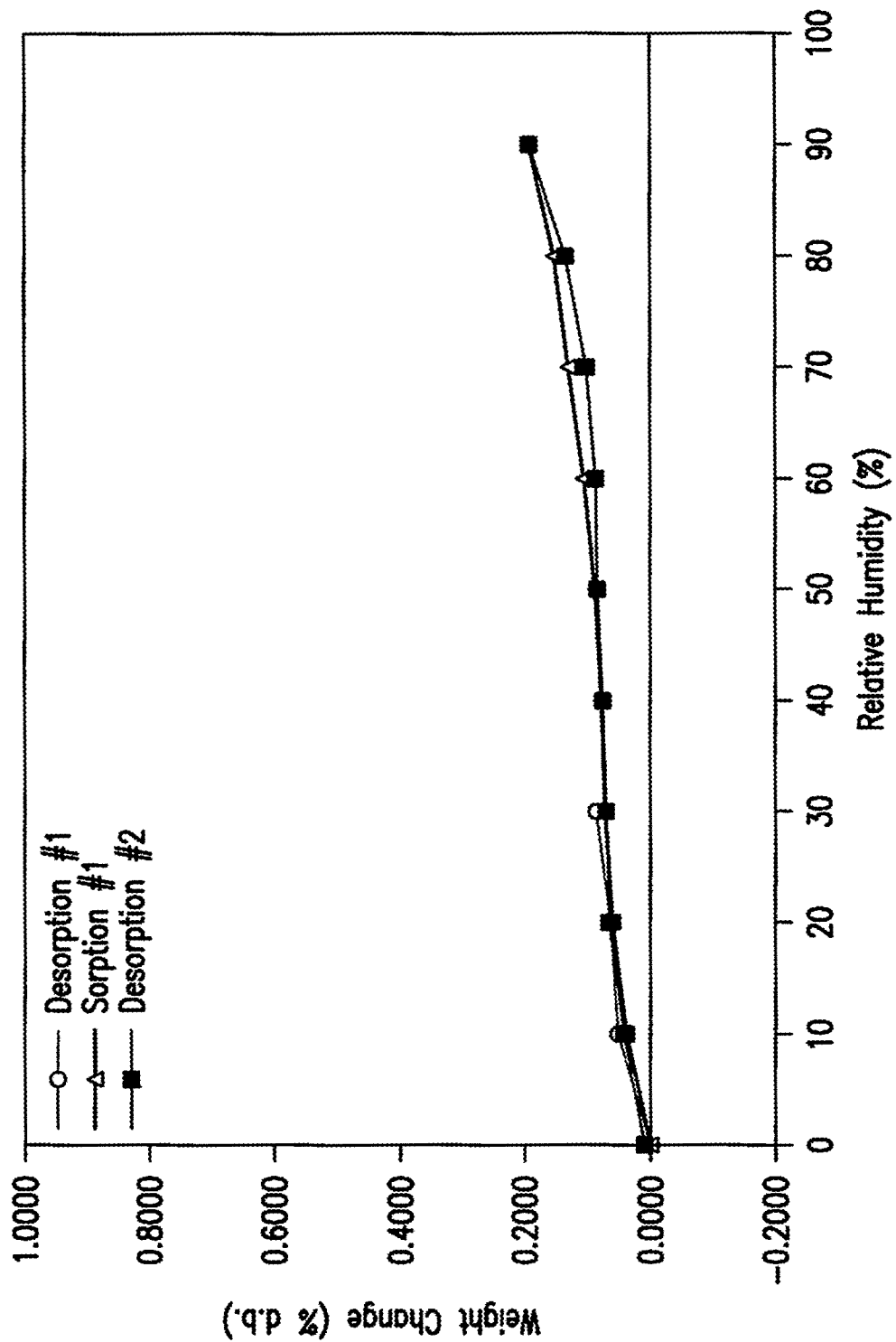
FIG. 3 is a moisture sorption isotherm of a crystalline monohydrate salt of (4s)-4-(5-phenyl-1,3,4-thiadiazol-2-yloxy)-1-azatricyclo[3.3.1.1$^{3,7}$]decane dihydrogen citrate, as determined by a dynamic moisture sorption balance, used to determine the hygroscopicity of the compound.

Further, the crystalline monohydrate salt of (4s)-4-(5-phenyl-1,3,4-thiadiazol-2-yloxy)-1-azatricyclo[3.3.1.1$^{3,7}$]decane dihydrogen citrate is generally considered non-hygroscopic, with a weight change ranging from 0.05% to 0.4%, for relative humidities ranging from 0% to 90%, as determined by dynamic moisture sorption balance. In a preferred embodiment, the weight change from 0% to 90% relative humidity is approximately 0.2%. The moisture sorption isotherm of (4s)-4-(5-phenyl-1,3,4-thiadiazol-2-yloxy)-1-azatricyclo[3.3.1.1$^{3,7}$]decane dihydrogen citrate monohydrate is illustrated in FIG. 3. Specifically, FIG. 3 illustrates the moisture sorption isotherm for the monohydrate salt at relative humidities ranging from 10% to 90%.

Moreover, the crystalline monohydrate of the current invention is a thermodynamically stable form of the salt under conditions of high water activity, high relative humidity, or high water activity and high relative humidity. Specifically, the crystalline monohydrate salt of (4s)-4-(5-phenyl-1,3,4-thiadiazol-2-yloxy)-1-azatricyclo[3.3.1.1$^{3,7}$]decane dihydrogen citrate is generally considered to have a critical water activity ranging from 0.05 to 0.20. In a preferred embodiment, the dihydrogen citrate monohydrate salt has a critical water activity between 0.10 and 0.15. As such, when the crystalline monohydrate of the current invention is exposed to relative humidity levels of less than 0.15, or other solvents with a water activity of 0.15, the salt may transform from the monohydrate form to the anhydrous form. If the crystalline monohydrate is exposed to relative humidities of 0.15 or greater, or solvents with a water activity greater than 0.15, the crystalline monohydrate salt of the current invention will remain thermodynamically stable, and will not convert to the anhydrous form of the compound. Accordingly, at relative humidities or water activities of 0.10 or less, solids of the current invention convert to the anhydrate form of the salt, whereas at relative humidities or water activities of 0.15 and above, the solids convert to the monohydrate form of the salt. Therefore, the crystalline monohydrate salt form of the current composition may be combined with solvents or other pharmaceutical carriers having a water activity greater than 0.15, as well as environments having a relative humidity greater than 0.15, and the crystalline monohydrate will not convert to the anhydrous form of the compound, ensuring thermodynamic stability. As it is used herein, the term "high humidity" or "high water activity" environments include all those with a relative humidity or water activity of 0.15 or greater. It should be noted that all water activity data was determined at ambient conditions. For the purposes of the water activity and all other parameters discussed herein, ambient conditions are generally defined to encompass a temperature of approximately 20° C. and a pressure of approximately one atmosphere.

FIG. 4 illustrates the stability of the current compound in environments of various water activities and relative humidities greater than 0.15. Specifically, FIG. 4 shows the powder X-ray diffraction pattern for various suspensions with varying water activities. Specifically, FIG. 4 illustrates the shift from the monohydrate salt to the anhydrous salt at a water activity ranging from 0.10 to 0.15. The methodology for the results in FIG. 4 is explained in greater detail in Example 6.

As used herein the term "substantially pure", when used in reference to the crystalline monohydrate salt of (4s)-4-(5-phenyl-1,3,4-thiadiazol-2-yloxy)-1-azatricyclo[3.3.1.1$^{3,7}$]decane dihydrogen citrate, refers to a salt that is greater than about 90% pure. The other forms of (4s)-4-(5-phenyl-1,3,4-thiadiazol-2-yloxy)-1-azatricyclo[3.3.1.1$^{3,7}$]decane dihydrogen citrate do not contain more than about 10% of any other compound and, in particular, does not contain more than about 10% of any other forms such as amorphous forms, anhydrous forms, solvated forms, non-solvated forms, desolvated forms, and the enantiomer.

More preferably, a "substantially pure" salt refers to a salt that is greater than about 95% pure, wherein the crystalline monohydrate salt of (4s)-4-(5-phenyl-1,3,4-thiadiazol-2-yloxy)-1-azatricyclo[3.3.1.1$^{3,7}$]decane dihydrogen citrate monohydrate does not contain more than about 5% of any other compound and, in particular, does not contain more than about 5% of any other form of (4s)-4-(5-phenyl-1,3,4-thiadiazol-2-yloxy)-1-azatricyclo[3.3.1.1$^{3,7}$]decane dihydrogen citrate monohydrate, such as amorphous forms, anhydrous forms, solvated forms, non-solvated forms, desolvated forms, and the enantiomer.

Even more preferably, a "substantially pure" salt refers to a salt that is greater than about 97% pure, wherein the crystalline monohydrate salt of (4s)-4-(5-phenyl-1,3,4-thiadiazol-2-yloxy)-1-azatricyclo[3.3.1.1$^{3,7}$]decane dihydrogen citrate monohydrate does not contain more than about 3% of any other compound and, in particular, does not contain more than about 3% of any other form of (4s)-4-(5-phenyl-1,3,4-thiadiazol-2-yloxy)-1-azatricyclo[3.3.1.1$^{3,7}$]decane dihydrogen citrate monohydrate, such as amorphous forms, anhydrous forms, solvated forms, non-solvated forms, desolvated forms, and the enantiomer.

As a general protocol, the various methods of chemical and physical analysis are included herein. Powder X-ray diffraction (PXRD) analysis of samples was conducted in the following manner. Samples for X-ray diffraction analysis were prepared by spreading the sample in a thin layer on the sample holder and gently flattening the sample with a microscope slide. For example, the sample may have been ground to a fine powder with mortar and pestle, or with glass microscope slides for limited quantity samples. Samples were run in one of three configurations: circular bulk holder, a quartz zero background plate, or hot stage mount (similar mounting to a zero background plate).

Diffraction patterns were collected using an Inel G3000 difractometer equipped with an incident beam germanium monochromator to provide Cu—K$_{\alpha 1}$ radiation. The X-ray generator was operated at a voltage of 40 kV and a current of 30 mA. The Inel G3000 is equipped with a position sensitive detector that monitors all diffraction data simultaneously. The detector was calibrated by collecting the attenuated direct beam for seven seconds in 1 degree intervals across a 90 degree two theta range. The calibration was checked against a silicon line position reference standard (NIST 640c). Samples were placed on an aluminum sample holder and leveled with a glass slide.

Alternatively, X-ray powder diffraction can be performed using a Rigaku Miniflex diffractometer (30 kV and 15 mA; X-ray source: Cu; Range: 2.00-40.00° Two Theta; Scan rate: 1-5 degree/minute) or a Scintag X1 or X2 diffractometer (2 kW normal focus X-ray tube with either a liquid nitrogen or Peltier cooled germanium solid state detector; 45 kV and 40 mA; X-ray source: Cu; Range: 2.00-40.00° Two Theta; Scan Rate: 1-5 degree/minute).

Characteristic powder X-ray diffraction pattern peak positions are reported in terms of angular positions (two theta) with an allowable variability of ±0.20°. The variability of ±0.10° is intended to be used when comparing two powder X-ray diffraction patterns. In practice, if a diffraction pattern peak from one pattern is assigned a range of angular positions (two theta) which is the measured peak position±0.20° and a diffraction pattern peak from another pattern is assigned a range of angular positions (two theta) which is measured peak position±0.20° and if those ranges of peak position overlap, then the two peaks are considered to have the same angular position (two theta). For example, if a diffraction pattern peak from one pattern is determined to have a peak position of 5.20° for comparison purposes the allowable variability allows the peak to be assigned a position in the range of 5.00°-5.40°. If a comparison peak from the other diffraction pattern is determined to have a peak position of 5.35° and the allowable variability allows the peak to be assigned a position in the range of 5.15°-5.55°, then the two peaks being compared are considered to have the same angular position (two theta) because there is overlap between the two ranges of peak positions.

Single crystal X-ray diffraction data were collected using a Bruker Apex II diffractometer (Bruker AXS, Madison, Wis.) equipped with an Apex II CCD area detector. The diffractometer was operated with a molybdenum anode tube (2.0 kW fine focus) at 50 kV and 40 mA. An incident beam silicon monochrometer provided Mo—K$_{\alpha 1}$ monochromatic radiation. The data were collected under a stream of cold nitrogen gas at 100 K using a Kryoflex low temperature device (Bruker AXS). The beam diameter for data collection was 5 mm and the detector distance was 6 cm. The alignment of the goniometer was checked using a spherical 2-Dimethylsufuranylidene-1,3-indanedione (YLID) crystal. The instrument was computer controlled using the BIS and Apex 2 software (Version 2008.5-0, Bruker AXS). Data were collected at −100° C.

Thermal gravimetric analysis (TGA) of samples was conducted in the following manner. TGA traces were collected on a thermal balance (Q-500), TA Instruments, New Castle, Del.) equipped with a data analyzer (Universal Analysis 2000, version 5.4A, TA Instruments). During experiments, the furnace was purged with nitrogen at 60 mL/min, while the balance chamber was purged at 40 mL/min. The temperature of the TGA furnace was calibrated using curie points of alumel and nickel. Generally, the experimental parameters included a sample weight of 2-20 mg, which was placed in an open aluminum pan; a heating rate of 10° C. per minute; and heating the sample from 25° C. to 200° C.

Dynamic moisture sorption balance (DMSB) was used to evaluate the hygroscopicity of the crystalline monohydrate compound. The hygroscopicity was evaluated using a dynamic moisture sorption balance (IGAsorp, Hiden Isochema) equipped with a data analyzer. The balance was calibrated using standardized weights of 20, 50, and 100 mg. The RH probe was calibrated using standardized salt solutions of lithium chloride, potassium carbonate, and sodium chloride. During the experiment, the flow rate of nitrogen gas at different relative humidity was 250 mL/min. For anhydrous materials, the sample was first dried with dry nitrogen at 50° C. for two hours. The temperature was then set to 25° C. and the relative humidity was changed from 0% to 90% and back to 0% at 10% intervals. For hydrated samples the temperature was set to 25° C. and the relative humidity was changed at 10% intervals from 30% to 90%, back to 10%, and then to 90%. For each step described herein, a one hour equilibration time period was used.

The critical water activity of the monohydrate salt can be determined by mixing different ratios of organic solvents and water. The analysis of the water activity for these solvent mixtures are temperature dependent. Determination of the critical water activity typically comprises the following steps: (1) preparation of solvent mixtures with a range of water activities; (2) saturation of the organic solvent/water mixtures with the monohydrate salt; (3) the optional filtration of the saturated solution; (4) addition of a 1:1 solid mixture (e.g., 25 mg/phase) of the anhydrous and hydrated phases to the saturated organic solvent/water mixtures; (5) equilibration at the temperature of interest (3-5 days); and (6) analysis of the residual solids by the appropriate technique, as understood by one skilled in the art (e.g., PXRD) to determine the identity of the stable phases.

Methods for Preparing Compounds of the Invention

The current invention also comprises methods for producing the compound (4s)-4-(5-phenyl-1,3,4-thiadiazol-2-yloxy)-1-azatricyclo[3.3.1.1$^{3,7}$]decane dihydrogen citrate monohydrate. The processes for developing the monohydrate form of the dihydrogen citrate salt can employ as starting material (4s)-4-(5-phenyl-1,3,4-thiadiazol-2-yloxy)-1-azatricyclo[3.3.1.1$^{3,7}$]decane. Alternatively, the dihydrogen citrate anhydrate compound can be used. As discussed in greater detail in the co-pending '336 publication, various methods of producing the compound (4s)-4-(5-phenyl-1,3, 4-thiadiazol-2-yloxy)-1-azatricyclo[3.3.1.1$^{3,7}$]decane free base and the dihydrogen citrate anhydrate compound are known, and are incorporated herein by reference. One skilled in the art will appreciate that alternative methods of producing the free base and dihydrogen citrate anhydrate forms of (4s)-4-(5-phenyl-1,3,4-thiadiazol-2-yloxy)-1-azatricyclo[3.3.1.1$^{3,7}$]decane according to conventional methods are also within the scope of the current invention.

As alluded to above, in one embodiment, the invention includes a method for producing (4s)-4-(5-phenyl-1,3,4-thiadiazol-2-yloxy)-1-azatricyclo[3.3.1.1$^{3,7}$]decane dihydrogen citrate monohydrate from a starting material comprising (4s)-4-(5-phenyl-1,3,4-thiadiazol-2-yloxy)-1-azatricyclo[3.3.1.1$^{3,7}$]decane. The method comprises the steps of: suspending a (4s)-4-(5-phenyl-1,3,4-thiadiazol-2-yloxy)-1-azatricyclo[3.3.1.1$^{3,7}$]decane dihydrogen citrate solid in a solvent; sealing the suspension for a sufficient amount of time to allow crystals to form; and harvesting or recovering the crystals from the suspension. Generally, the method is performed under ambient conditions (room temperature); however, one skilled in the art can adjust the temperature as necessary to achieve the desired or alternative results. Generally, the solvents of the current invention incorporate a combination of water and at least one other solvent. The combination of water and at least one other solvent typically has a critical water activity of greater than 0.10. Suitable solvents that can be combined with water in this method include, but are not limited to, an aliphatic alcohol (as used herein, an "aliphatic alcohol" refers to a lower alkyl alcohol with the phrase "lower alkyl" referring to a $C_1$-$C_6$ alkyl. Examples of aliphatic alcohols include, but are not limited to, methanol, ethanol, 2-propanol (IPA, also known as isopropanol), butanol, etc.), butanol acetonitrile (ACN), acetone, formamide, dimethyl formamide (DMF), toluene, benzene, anisole, ethyl acetate, isopropyl acetate (IPAc), tetrahydrofuran (THF), 1,4-dioxane, methyl tert-butyl ether (MTBE), dichloromethane, chloroform, hexanes, n-heptane, 2-butanone (MEK), dimethyl sulfoxide (DMSO), nitromethane, 1-methyl-2-pyrrolidone (NMP), triethylamine, tributylamine, trifluorotoluene, ethyl acetate, formamide/ethanol mixtures (1:1), formamide/IPA mixtures (1:1), formamide/ACN mixtures (1:1), formamide/MEK mixtures (1:1), formamide/ethyl acetate mixtures (1:1), formamide/THF mixtures (1:1), DMSO/methane mixtures (1:1), DMSO/IPA mixtures (1:1), DMSO/ACN mixtures (1:1), DMSO/MEK mixtures (1:1), DMSO/toluene mixtures (1:1), DMSO/ethyl acetate mixtures (1:1), DMSO/THF mixtures (1:1), DMSO/dichloromethane mixtures (1:1), formamide/ethanol mixtures (1:3), formamide/ACN mixtures (1:3), formamide/MEK mixtures (1:3), formamide/ethyl acetate mixtures (1:3), formamide/THF mixtures (1:3), DMSO/nitromethane mixtures (1:3), DMSO/ethanol mixtures (1:3), DMSO/ACN mixtures (1:3), DMSO/MEK mixtures (1:3), DMSO/toluene mixtures (1:3), DMSO/ethyl acetate mixtures (1:3), DMSO/THF mixtures (1:3), DMSO/dichloromethane mixtures (1:3), and combinations thereof. In a further embodiment, the solvent comprises a combination of water with methanol, ethanol, 2-propanol, and butanol.

In an additional embodiment, the invention encompasses a process for preparing a crystalline monohydrate salt of (4s)-4-(5-phenyl-1,3,4-thiadiazol-2-yloxy)-1-azatricyclo[3.3.1.1$^{3,7}$]decane dihydrogen citrate comprising the steps of: (a) dissolving the (4s)-4-(5-phenyl-1,3,4-thiadiazol-2-yloxy)-1-azatricyclo[3.3.1.1$^{3,7}$]decane in a combination of water and at least one solvent at a temperature ranging from approximately 65° C. to approximately 85° C.; (b) adjusting the temperature of the solution to a temperature ranging from approximately 55° C. to approximately 75° C. over a period of approximately thirty minutes to approximately eight hours; (c) adding at least one additional solvent to the solution and mixing for a period of approximately thirty minutes to approximately eight hours; (d) adjusting the temperature of the solutions to a temperature ranging from approximately 30° C. to approximately 50° C. over a period of approximately thirty minutes to approximately eight hours; (e) adding at least one additional solvent to the solution over a period of approximately thirty minutes to approximately eight hours; (f) maintaining the slurry at a temperature ranging from approximately 30° C. to approximately 50° C. for a period of approximately thirty minutes to approximately eight hours; (g) adjusting the temperature of the slurry to a temperature ranging from approximately −5° C. to approximately 15° C.; (h) mixing the slurry for a period of time ranging from approximately thirty minutes to approximately eight hours; and (i) extracting the crystalline monohydrate salt of (4s)-4-(5-phenyl-1,3,4-thiadiazol-2-yloxy)-1-azatricyclo[3.3.1.1$^{3,7}$]decane dihydrogen citrate.

In step (a) of the process, one skilled in the art will appreciate that the (4s)-4-(5-phenyl-1,3,4-thiadiazol-2-yloxy)-1-azatricyclo[3.3.1.1$^{3,7}$]decane used in the method can be a crude solid of (4s)-4-(5-phenyl-1,3,4-thiadiazol-2-yloxy)-1-azatricyclo[3.3.1.1$^{3,7}$]decane, pure (4s)-4-(5-phenyl-1,3,4-thiadiazol-2-yloxy)-1-azatricyclo[3.3.1.1$^{3,7}$]decane, or substantially pure (4s)-4-(5-phenyl-1,3,4-thiadiazol-2-yloxy)-1-azatricyclo[3.3.1.1$^{3,7}$]decane. Also in step (a) of the process, one skilled in the art will appreciate that a variety of solvents and combination of solids may be incorporated to dissolve the (4s)-4-(5-phenyl-1,3,4-thiadiazol-2-yloxy)-1-azatricyclo[3.3.1.1$^{3,7}$]decane. The solvent component generally comprises the combination of water with at least one other solvent. The combination of water and at least one other solvent typically has a critical water activity of greater than 0.10. Suitable solvents that can be combined with water in this method include, but are not limited to, an aliphatic alcohol (such as, but not limited to, methanol, ethanol, 2-propanol (IPA), butanol), butanol acetonitrile (ACN), acetone, formamide, dimethyl formamide (DMF), toluene, benzene, anisole, ethyl acetate, isopropyl acetate (IPAc), tetrahydrofuran (TEM), 1,4-dioxane, methyl tert-butyl ether (MTBE), dichloromethane, chloroform, hexanes, n-heptane, 2-butanone (MEK), dimethyl sulfoxide (DMSO), nitromethane, 1-methyl-2-pyrrolidone (NMP), triethylamine, tributylamine, trifluorotoluene, ethyl acetate, formamide/ethanol mixtures (1:1), formamide/IPA mixtures (1:1), formamide/ACN mixtures (1:1), formamide/MEK mixtures (1:1), formamide/ethyl acetate mixtures (1:1), formamide/THF mixtures (1:1), DMSO/methane mixtures (1:1), DMSO/IPA mixtures (1:1), DMSO/ACN mixtures (1:1), DMSO/MEK mixtures (1:1), DMSO/toluene mixtures (1:1), DMSO/ethyl acetate mixtures (1:1), DMSO/THF mixtures (1:1), DMSO/dichloromethane mixtures (1:1), formamide/ethanol mixtures (1:3), formamide/ACN mixtures (1:3), formamide/MEK mixtures (1:3), formamide/ethyl acetate mixtures (1:3), formamide/THF mixtures (1:3), DMSO/nitromethane mixtures (1:3), DMSO/ethanol mixtures (1:3), DMSO/ACN mixtures (1:3), DMSO/MEK mixtures (1:3), DMSO/toluene mixtures (1:3), DMSO/ethyl acetate mixtures (1:3), DMSO/THF mixtures (1:3), DMSO/dichloromethane mixtures (1:3), and combinations thereof. In another embodiment, the solvent comprises a combination of water with methanol, ethanol, 2-propanol, and butanol. In a further preferred embodiment, the solvent comprises a mixture of 2-propanol and water. The mixture of the at least one other solvent and water generally comprises a ratio of approximately 20:1 to approximately 1:10, respectively. In a preferred embodiment, the mixture of at least one other solvent and water comprises a ratio of approximately 1:1 to approximately 7:1, respectively. In a more preferred embodiment the mixture of 2-propanol and water comprises a ratio of approximately 4:1. Further, in another embodiment, step (a) of the process is performed at a temperature ranging from approximately 70° C. to approximately 80° C.

In a preferred embodiment, step (a) is performed at a temperature ranging from approximately 74° C. to approximately 76° C.

Step (b) of the process, as described previously involves cooling the temperature of the solution. In a preferred embodiment of step (b) of the process, the temperature of the solution is reduced to a temperature ranging from approximately 60° C. to approximately 70° C. over a period of approximately thirty minutes to approximately eight hours. However, one skilled in the art will understand that the length of time may be modified to less than approximately 30 minutes or greater than approximately eight hours without departing from the scope of the invention. In a more preferred embodiment of step (b) of the process, the temperature of the solution is reduced to a temperature ranging from approximately 64° C. to approximately 66° C.

In step (c) of the process, one skilled in the art will again appreciate that a variety of solvents (namely, one or more than one) may be incorporated into the solution. Suitable examples of solvents that may be incorporated into step (c) have been described previously above in connection with step (a), and are incorporated herein by reference. In a preferred embodiment, the solvent comprises an aliphatic alcohol (such as, but not limited to, methanol, ethanol, 2-propanol, butanol), water, and mixtures thereof. In a further preferred embodiment, the solvent comprises 2-propanol. The amount of solvent added during step (c) of the process generally ranges from about 1 volume to about 10 volumes, relative to the amount of solvent incorporated during step (a). In a preferred embodiment, the amount of solvent added during step (c) of the process generally ranges from about 2 volumes to about 8 volumes, relative to the amount of solvent added during step (a). In a most preferred embodiment, the amount of solvent added during step (c) of the process generally ranges from about 5 volumes to about 7 volumes, relative to the amount of solvent added during step (a).

Step (d) of the process involves a second phase in which the solution is cooled after mixing the additional solvent, as described in step (c). In a preferred embodiment, of step (d), the temperature of the solution is reduced to a temperature ranging from approximately 35° C. to approximately 45° C. over a period of approximately thirty minutes to approximately eight hours. One skilled in the art will understand that the length of time may be modified to less than approximately 30 minutes or greater than approximately eight hours without departing from the scope of the invention. In a more preferred embodiment of step (d), the temperature of the solution is reduced to a temperature ranging from approximately 39° C. to approximately 41° C.

Step (e) of the process comprises adding at least one solvent to the solution over a period ranging from approximately 30 minutes to approximately eight hours. As stated previously, the skilled artisan will appreciate that the length of time may be modified to less than approximately 30 minutes or greater than approximately eight hours without departing from the scope of the invention Suitable examples of solvents that may be incorporated into step (c) have been described previously above in connection with step (a) and are incorporated herein by reference. In a preferred embodiment, the solvent comprises an aliphatic alcohol (such as, but not limited to, methanol, ethanol, 2-propanol, butanol), water, and mixtures thereof. In a further preferred embodiment, the solvent comprises 2-propanol. The amount of solvent added during step (e) of the process generally ranges from about 1 volume to about 10 volumes, relative to the amount of solvent incorporated during step (a). In a preferred embodiment, the amount of solvent added during step (e) of the process generally ranges from about 2 volumes to about 8 volumes, relative to the amount of solvent incorporated during step (a). In a most preferred embodiment, the amount of solvent added during step (e) of the process generally ranges from about 4 volumes to about 6 volumes, relative to the amount of solvent incorporated during step (a).

Step (f) of the process is directed to maintaining the temperature of the slurry after addition of the solvent in step (e). One skilled in the art will appreciate that the maintenance of the temperature in step (f) should coincide with the temperature established in step (d).

Step (g) of the process involves cooling the slurry formulation to a temperature ranging from approximately −5° C. to approximately 15° C. over a period of approximately thirty minutes to approximately eight hours. However, one skilled in the art will understand that the length of time may be modified to less than approximately 30 minutes or greater than approximately eight hours without departing from the scope of the invention. In a preferred embodiment of step (g), the temperature of the solution is reduced to a temperature ranging from approximately 0° C. to approximately 10° C. In a more preferred embodiment of step (d), the temperature of the solution is reduced to a temperature ranging from approximately 4° C. to approximately 6° C.

Step (h) of the process involves the mixing of the cooled slurry for a period ranging from about thirty minutes to about eight hours. One having skill in the art will appreciate the time period for mixing may be altered depending upon the reaction conditions, without departing from the scope of the invention. One skilled in the art will appreciate that any means of mixing known in the art may be used, including both manual and automated forms of mixing the slurry.

Finally, step (i) of the process is directed to recovering (such as by extracting) the crystalline monohydrate salt of (4s)-4-(5-phenyl-1,3,4-thiadiazol-2-yloxy)-1-azatricyclo[3.3.1.1$^{3,7}$]decane dihydrogen citrate from the slurry solution. In a preferred embodiment, the method of recovery (extraction) comprises the additional steps of drying and filtration. The skilled artisan will understand that the process of drying and filtering the crystals may be performed by any method known in the art. Generally, the recovery process comprises a drying time ranging from approximately one hour to approximately twenty-four hours, at a temperature ranging from approximately 40° C. to approximately 70° C.

In a further embodiment, the current invention comprises a method for producing the crystalline monohydrate salt of (4s)-4-(5-phenyl-1,3,4-thiadiazol-2-yloxy)-1-azatricyclo[3.3.1.1$^{3,7}$]decane dihydrogen citrate, using the anhydrous form of the compound as a starting material. This method comprises the steps of: (a) contacting anhydrous (4s)-4-(5-phenyl-1,3,4-thiadiazol-2-yloxy)-1-azatricyclo[3.3.1.1$^{3,7}$]decane dihydrogen citrate solid with a solvent comprising a combination of water and at least one other solvent, wherein the combination has a water activity greater than 0.1, in a reaction vessel; (b) sealing the reaction vessel and protecting the suspension from light at ambient conditions; and (c) recovering the crystalline monohydrate salt of (4s)-4-(5-phenyl-1,3,4-thiadiazol-2-yloxy)-1-azatricyclo[3.3.1.1$^{3,7}$]decane. Processes for the production of the anhydrate of (4s)-4-(5-phenyl-1,3,4-thiadiazol-2-yloxy)-1-azatricyclo[3.3.1.1$^{3,7}$]decane dihydrogen citrate are disclosed in pending United States Publication No. 2008/0167336, which is hereby fully incorporated by reference. The solvent used in step (a) of the process is generally defined as any organic solvent, water, or a mixture thereof, capable of dissolving the anhydrous salt of (4s)-4-(5-phenyl-1,3,4-thiadiazol-2-yloxy)-1-azatricyclo[3.3.1.1$^{3,7}$]decane dihydrogen citrate. Suitable examples of solvents that may be used in the claimed process include, but are not limited to, an aliphatic alcohol (such as, but not limited to, methanol, ethanol, 2-propanol, butanol, etc.), butanol acetonitrile, acetone, formamide, dimethyl formamide, toluene, benzene, anisole, ethyl acetate, isopropyl acetate, tetrahydrofuran, 1,4-dioxane, methyl tert-butyl ether, dichloromethane, chloroform, hexanes, n-heptane, 2-butanone, dimethyl sulfoxide, nitromethane, 1-methyl-2-pyrrolidone, triethylamine, tributylamine, trifluorotoluene, water, and mixtures thereof. In a preferred embodiment, the solvent comprises water. In another preferred embodiment, the solvent comprises a mixture of an organic solvent and water, whereby the organic solvent may comprise any of those previously cited.

One skilled in the art will appreciate that the amount of anhydrous solid used in the process described above will vary depending on the exact parameters sought by the skilled artisan. Accordingly, the amount of anhydrous solvent mixed with the solvent will vary according to the particular solvent chosen. In general, the amount of anhydrous solid may range from approximately 1 mg to approximately 1000 mg of anhydrous solid per mL of solvent. In a preferred embodiment, the amount of anhydrous solid may range from approximately 10 mg to approximately 500 mg of anhydrous solid per mL of solvent. In a more preferred embodiment, the amount of anhydrous solid is approximately 90 mg per mL of solvent. Additionally, the current process uses 5-volumes of solvent to dissolve anhydrous solid at a high temperature ranging from approximately 40° C. to approximately 70° C. The solution is then cooled to ambient temperature and the solution is allowed to seed. Subsequently, 6 volumes of antisolvent are then added (making a total of 11 volumes of solvent), the crystallization slurry is again cooled and the crystals are harvested. One skilled in the art will appreciate that the antisolvent may comprise any solvent capable of decreasing the solubility of the solution, consequently promoting crystal formation.

It will be further understood by the skilled artisan that any reaction vessel capable of holding the reaction mixture, while not affecting the reaction will be acceptable in the current invention. Further, the reaction vessel may be sealed to protect the reaction mixture from light at ambient conditions, by any means known in the art, including parafilm. Additionally, the skilled artisan will appreciate that the reaction is allowed to proceed for an amount of time sufficient to allow for the transformation from the anhydrous form to the crystalline monohydrate form of the compound. As noted earlier, ambient conditions are generally defined as a temperature of approximately 20° C. and a pressure of approximately one atmosphere.

Finally, one skilled in the art will appreciate that the monohydrate crystals of (4s)-4-(5-phenyl-1,3,4-thiadiazol-2-yloxy)-1-azatricyclo[3.3.1.1$^{3,7}$]decane dihydrogen citrate may be recovered by any method known within the art. Specific examples of recovery methods include filtration and drying methods. The method of filtration and the time and temperature of drying may vary according to known methods.

Pharmaceutical Compositions of the Invention

The invention also provides pharmaceutical compositions comprising a therapeutically effective amount of (4s)-4-(5-phenyl-1,3,4-thiadiazol-2-yloxy)-1-azatricyclo[3.3.1.1$^{3,7}$]decane dihydrogen citrate monohydrate in combination with a pharmaceutically acceptable carrier. The compositions comprise compounds of the invention formulated together with one or more non-toxic pharmaceutically acceptable carriers. One skilled in the art will appreciate that the therapeutically effective amount of (4s)-4-(5-phenyl-1,3,4-thiadiazol-2-yloxy)-1-azatricyclo[3.3.1.1$^{3,7}$]decane dihydrogen citrate monohydrate may vary depending on the type of application envisioned for the pharmaceutical product. However, in preferred embodiments, the concentration of (4s)-4-(5-phenyl-1,3,4-thiadiazol-2-yloxy)-1-azatricyclo [3.3.1.1$^{3,7}$]decane dihydrogen citrate monohydrate ranges from approximately 0.1% to approximately 99% by weight of the composition.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofuranyl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of (4s)-4-(5-phenyl-1,3,4-thiadiazol-2-yloxy)-1-azatricyclo[$3.3.1.1^{3,7}$] decane dihydrogen citrate monohydrate, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention also contemplates pharmaceutically acceptable compounds that when administered to a patient in need may be converted through in vivo biotransformation into compounds of formula (I).

Determination of Biological Activity

To determine the effectiveness of (4s)-4-(5-phenyl-1,3,4-thiadiazol-2-yloxy)-1-azatricyclo[$3.3.1.1^{3,7}$]decane dihydrogen citrate monohydrate as a ligand for $\alpha 7$ nAChRs, the compounds of the invention was evaluated according to the [$^3$H]-methyllycaconitine (MLA) binding assay, or the [$^3$H]-DPPB binding assay. To determine the effectiveness of representative compounds of this invention as ligands for $\alpha 4\beta 2$ nAChRs, the compound of the invention was evaluated according to the [$^3$H]-cytisine binding assay, which was performed as described below.

[$^3$H]-Cytisine Binding

Binding to the $\alpha 4\beta 2$ nAChR subtype was determined according to conditions which were modified from the procedures described in Pabreza L A, Dhawan, S, Kellar K J, [$^3$H]-Cytisine Binding to Nicotinic Cholinergic Receptors in Brain, Mol. Pharm. 39: 9-12, 1991. Membrane enriched fractions from rat brain minus cerebellum (ABS Inc., Wilmington, Del.) were slowly thawed at 4° C., washed and resuspended in 30 volumes of BSS-Tris buffer (120 mM NaCl/5 mM KCl/2 mM CaCl$_2$/2 mM MgCl$_2$/50 mM Tris-Cl, pH 7.4, 4° C.). Samples containing 100-200 µg of protein and 0.75 nM [$^3$H]-cytisine (30 C$_i$/mmol; Perkin Elmer/NEN Life Science Products, Boston, Mass.) were incubated in a final volume of 500 µL for 75 minutes at 4° C. Seven log-dilution concentrations of each compound were tested in duplicate. Non-specific binding was determined in the presence of 10 µM (−)-nicotine. Bound radioactivity was isolated by vacuum filtration onto prewetted glass fiber filter plates (Millipore, Bedford, Mass.) using a 96-well filtration apparatus (Packard Instruments, Meriden, Conn.) and were then rapidly rinsed with 2 mL of ice-cold BSS buffer (120 mM NaCl/5 mM KCl/2 mM $CaCl_2$/2 mM $MgCl_2$). Packard MicroScint-20® scintillation cocktail (40 µL) was added to each well and radioactivity determined using a Packard TopCount® instrument. The $IC_{50}$ values were determined by nonlinear regression in Microsoft Excel® software. $K_i$ values were calculated from the $IC_{50}$s using the Cheng-Prusoff equation, where $K_i=IC_{50}/(1+[Ligand]/K_D)$.

[$^3$H]-Methyllycaconitine (MLA) Binding

Binding to the α7 nAChR subtype was determined according to conditions which were similar to those used for the [$^3$H]-cytisine binding assay. Membrane enriched fractions from rat brain minus cerebellum (ABS Inc., Wilmington, Del.) were slowly thawed at 4° C., washed and resuspended in 30 volumes of BSS-Tris buffer (120 mM NaCl, 5 mM KCl, 2 mM $CaCl_2$, 2 mM $MgCl_2$, and 50 mM Tris-Cl, pH 7.4, 22° C.). Samples containing 100-200 µg of protein, 5 nM [$^3$H]-MLA (25 $C_i$/mmol; Perkin Elmer/NEN Life Science Products, Boston, Mass.) and 0.1% bovine serum albumin (BSA, Millipore, Bedford, Mass.) were incubated in a final volume of 500 µL for 60 minutes at 22° C. Seven log-dilution concentrations of each compound were tested in duplicate. Non-specific binding was determined in the presence of 10 µM MLA. Bound radioactivity was isolated by vacuum filtration onto glass fiber filter plates prewetted with 2% BSA using a 96-well filtration apparatus (Packard Instruments, Meriden, Conn.) and were then rapidly rinsed with 2 mL of ice-cold BSS. Packard MicroScint-20® scintillation cocktail (40 µL) was added to each well and radioactivity was determined using a Packard TopCount® instrument. The $IC_{50}$ values were determined by nonlinear regression in Microsoft Excel® software. $K_i$ values were calculated from the $IC_{50}$s using the Cheng-Prusoff equation, where $K_i=IC_{50}/(1+[Ligand]/K_D)$.

[$^3$H]-DPPB Binding

[$^3$H]-DPPB, [$^3$H]-(S,S)-2,2-dimethyl-5-(6-phenyl-pyridazin-3-yl)-5-aza-2-azonia-bicyclo[2.2.1]heptane iodide, binding to the α7 nAChR subtype was determined using membrane enriched fractions from rat brain minus cerebellum or human cortex (ABS Inc., Wilmington, Del.). Pellets were thawed at 4° C., washed and resuspended with a Polytron at a setting of 7 in 30 volumes of BSS-Tris buffer (120 mM NaCl, 5 mM KCl, 2 mM $CaCl_2$, 2 mM $MgCl_2$, and 50 mM Tris-Cl, pH 7.4, 4° C.). Seven log-dilution concentrations of test compounds containing 100-200 µg of protein, and 0.5 nM [$^3$H]-DPPB (62.8 Ci/mmol; R46V, Abbott Labs) were incubated in a final volume of 500 µl for 75 minutes at 4° C. in duplicate. Non-specific binding was determined in the presence of 10 µM methyllycaconitine. Bound radioactivity was collected on Millipore MultiScreen® harvest plates FB presoaked with 0.3% PEI using a Packard cell harvester, washed with 2.5 ml ice-cold buffer, and radioactivity was determined using a Packard TopCount Microplate beta counter. $IC_{50}$ values were determined by nonlinear regression in Microsoft® Excel or Assay Explorer. $K_i$ values were calculated from the $IC_{50}$s using the Cheng-Prusoff equation, where $K_i=IC_{50}/(1+[Ligand]/K_D)$. [$^3$H]-DPPB was obtained according to the preparation procedures described below.

[Methyl-$^3$H]2,2-Dimethyl-5-(6-phenyl-pyridazin-3-yl)-5-aza-2-azonia-bicyclo[2.2.1]heptane; iodide Preparation

[Methyl-$^3$H]2,2-dimethyl-5-(6-phenyl-pyridazin-3-yl)-5-aza-2-azonia-bicyclo[2.2.1]heptane; iodide used in the [$^3$H]-DPPB binding assay above was prepared according to the following procedures.

Step 1: Preparation of t-Butyl(S,S)-5-(6-Phenyl-pyridazin-3-yl)-2,5-diazabicyclo[2.2.1]heptane-2-carboxylate Triethylamine (20 mL) was added to a suspension of t-butyl(S,S)-2,5-diazabicyclo[2.2.1]heptane-2-carboxylate (3.43 g, 17.3 mmol, Aldrich Chemical Company) and 3-chloro-6-phenylpyridazine (3.30 g, 17.3 mmol, Aldrich Chemical Company) in toluene (50 mL) and the mixture was heated under nitrogen at 100° C. for 7 days. The dark mixture was cooled to room temperature, and the resulting precipitate was isolated by filtration, washed with toluene (15 mL) and dried under vacuum to provide the title compound as an off-white solid (3.00 g). The filtrate was concentrated and the residue was purified by column chromatography on silica gel, eluting with ethyl acetate, to provide additional product (0.41 g, total yield 3.41 g, 56%): MS (DCl/$NH_3$) m/z 353 $(M+H)^+$.

Step 2: Preparation of (S,S)-2-Methyl 5-(6-phenyl-pyridazin-3-yl)-2,5-diazabicyclo[2.2.1]heptane The product obtained from Step 1 (3.41 g, 9.7 mmol) was dissolved in formic acid (20 mL) and treated with formalin (37% by weight, 1.0 g, 12.3 mmol). The mixture was heated at 100° C. for 1 hour, and the brown solution was cooled to room temperature and concentrated under vacuum. The residue was purified by column chromatography on silica gel, eluting with $CH_2Cl_2$—$CH_3OH$—$NH_4OH$ (95:5:1) to provide the title compound as an off-white solid (2.50 g, 96%): MS (DCl/$NH_3$) m/z 267 $(M+H)^+$.

Step 3: Preparation of [$^3$H]-(S,S)-2,2-Dimethyl-5-(6-phenyl-pyridazin-3-yl)-5-aza-2-azonia-bicyclo [2.2.1]heptane iodide ([$^3$H]-DPPB)

[$^3$H]Methyl iodide in toluene (250 mCi in 0.1 mL, 85 Ci/mmol, American Radiolabeled Chemicals, Inc.) was combined with a solution of the product obtained from Step 2 in dichloromethane (0.788 mg, 2.96 µmole in 0.45 mL). The vial was capped and the mixture was allowed to react overnight at room temperature. Methanol was added and the solvents were evaporated to give 42 mCi. The product was taken up in methanol for HPLC purification.

Step 4: Purification by High Performance Liquid Chromatography (HPLC)

About 7 mCi of [$^3$H]-DPPB was evaporated to dryness and the residue was dissolved in total about 4.5 ml acetonitrile:water:TFA (15:85:0.1). Approximately 0.9 mL per injection were made onto a Phenomenex Luna C18(2) column (5 micron, 250 mm×4.6 mm ID) using an Agilent HPLC system. [$^3$H]-DPPB was eluted by a gradient mobile phase from 10% B to 20% B in 20 min where Mobile Phase A=0.1% trifluoroacetic acid in water and Mobile Phase B=0.1% trifluoroacetic acid in acetonitrile at a flow rate of approximately 1 mL/min. Peak detection and chromatograms were obtained with an Agilent variable wavelength UV detector set at 275 nm. The fractions containing [$^3$H]-DPPB were collected at approximately 14 minutes using an Agilent fraction collector. The fractions were combined and the solvents were evaporated in vacuo. The residue was dissolved in 200 proof ethanol (2 mL) to give 0.7 mCi.

Step 5: Determination of Purity and Specific Activity

[$^3$H]-DPPB was assayed using an Agilent 1100 series HPLC system consisting of a quaternary pump, an autosampler, and a photodiode array UV detector. A Packard Radiomatic A 500 radioactivity detector was connected to the HPLC system. For radiodetection, a 500 µL flow cell and a 3:1 ratio of Ultima-Flo M scintillation cocktail to HPLC mobile phase were used. The analyses were performed using a Phenomenex Luna C18(2) column (5 microns, 250 mm×4.6 mm ID). The mobile phase consisted of a gradient starting with 10% B and ramping to 20% B in 20 minutes followed by ramping to 90% B in 1 minute and hold at 90% B for 9 minutes, where Mobile Phase A=0.1% trifluoroacetic acid in water and Mobile Phase B=0.1% trifluoroacetic acid in acetonitrile. The flow rate was set at approximately 1 mL/min and the UV detection was set at 275 nm.

Preferred compounds of the invention had $K_i$ values of from about 0.1 nanomolar to about 10 micromolar when tested by the [$^3$H]-MLA assay, many having a $K_i$ of less than 1 micromolar. Other preferred compounds demonstrated [$^3$H]-Cytisine binding values of compounds of the invention ranged from about 0.1 nanomolar to at least 10 micromolar. Some preferred compounds exhibited greater potency at α7 receptors compared to α4β2 receptors. The determination of such preferred compounds typically considered the $K_i$ value as measured by MLA assay in view of the $K_i$ value as measured by [$^3$H]-cytisine binding, such that in the formula $D = K_{i\ H\text{-}cytisine}^3 / K_{i\ MLA}$, D is greater than about 50. Alternatively, the $K_i$ value as measured by [$^3$H]-DPPB assay can be used in place of the $K_{i\ MLA}$ such that in the formula $D = K_{i\ H\text{-}cytisine}^3 / K_{i\ [3H]\text{-}DPPB}$, D' is greater than about 50.

Compounds of the invention are α7 nAChRs ligands and/or α4β2 ligands that modulate function of α7 nAChRs and/or α4β2 ligands by altering the activity of the receptor or signaling. The compounds can be inverse agonists that inhibit the basal activity of the receptor or antagonists that completely block the action of receptor-activating agonists. The compounds also can be partial agonists that partially block or partially activate the α7 nAChR receptor or agonists that activate the receptor. Binding to the α7 nicotinic receptor also triggers key signaling processes involving various kinases and phosphatases and protein-protein interactions that are important to effects on memory, cytoprotection, gene transcription and disease modification.

Methods of the Invention

Compounds and compositions of the invention are useful for modulating the effects of nAChRs, and more particularly α7 nAChRs. In particular, the compounds and compositions of the invention can be used for treating or preventing disorders modulated by α7 nAChRs. Typically, such disorders can be ameliorated by selectively modulating the α7 nAChRs in a mammal, preferably by administering a compound or composition of the invention, either alone or in combination with another active agent, for example, as part of a therapeutic regimen.

In addition, the invention relates to a method for treating or preventing conditions, disorders or deficits modulated by an α7 nicotinic acetylcholine receptor, an α4β2 nicotinic acetylcholine receptor or both α7 and α4β2 nicotinic acetylcholine receptor wherein the condition, disorder, or deficit is selected from the group consisting of a memory disorder, cognitive disorder, neurodegeneration, or neurodevelopmental disorder, or a combination thereof comprising administration of a therapeutically suitable amount of the crystalline salt of (4s)-4-(5-phenyl-1,3,4-thiadiazol-2-yloxy)-1-azatricyclo[3.3.1.1$^{3,7}$]decane having formula (I)

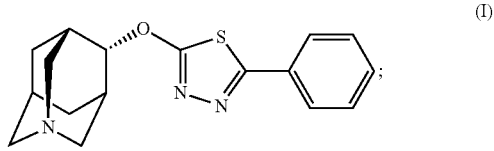 [SMILES: c1ccc(-c2nnc(O[C@@H]3C4CC5C[C@H]3C[N@](C5)C4)s2)cc1]

(I)

wherein the salt comprises dihydrogen citrate having formula (II)

(2)

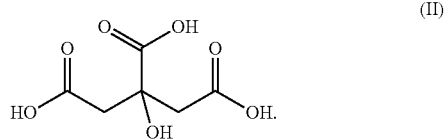

(II)

The invention also contemplates the method for treating or preventing a condition or disorder modulated by an α7 nicotinic acetylcholine receptor comprising the step of administering the compound (4s)-4-(5-phenyl-1,3,4-thiadiazol-2-yloxy)-1-azatricyclo[3.3.1.1$^{3,7}$]decane dihydrogen citrate monohydrate, wherein the condition or disorder is selected from a memory disorder, cognitive disorder, neurodegeneration, and neurodevelopmental disorder.

The invention also contemplates a method for treating or preventing a condition or disorder modulated by an α7 nicotinic acetylcholine receptor comprising the step of administering the compound (4s)-4-(5-phenyl-1,3,4-thiadiazol-2-yloxy)-1-azatricyclo[3.3.1.1$^{3,7}$]decane dihydrogen citrate monohydrate, wherein the condition or disorder is selected from attention deficit disorder, attention deficit hyperactivity disorder (ADHD), Alzheimer's disease (AD), mild cognitive impairment, schizophrenia, senile dementia, AIDS dementia, Pick's disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain and inflammatory pain.

The invention also contemplates a method for treating or preventing a condition or disorder modulated by an α7 nicotinic acetylcholine receptor comprising the step of administering the compound (4s)-4-(5-phenyl-1,3,4-thiadiazol-2-yloxy)-1-azatricyclo[3.3.1.1$^{3,7}$]decane dihydrogen citrate monohydrate, wherein the condition or disorder is schizophrenia.

The invention also contemplates a method for treating or preventing a condition or disorder modulated by an α7 nicotinic acetylcholine receptor comprising the step of administering the compound (4s)-4-(5-phenyl-1,3,4-thiadiazol-2-yloxy)-1-azatricyclo[3.3.1.1$^{3,7}$]decane dihydrogen citrate monohydrate in combination with an atypical antipsychotic.

The invention also contemplates a method for treating or preventing a condition or disorder modulated by an α7 nicotinic acetylcholine receptor comprising the step of administering the compound (4s)-4-(5-phenyl-1,3,4-thiadiazol-2-yloxy)-1-azatricyclo[3.3.1.1$^{3,7}$]decane dihydrogen citrate monohydrate, wherein the condition or disorder is infertility, lack of circulation, need for new blood vessel growth associated with wound healing, more particularly circulation around a vascular occlusion, need for new blood vessel growth associated with vascularization of skin grafts, ischemia, inflammation, particularly those associated with rheumatoid arthritis, wound healing, and other complications associated with diabetes.

The invention also contemplates a method for treating or preventing a condition or disorder modulated both by α7 and α4β2 nicotinic acetylcholine receptors comprising the step of administering the compound (4s)-4-(5-phenyl-1,3,4-thiadiazol-2-yloxy)-1-azatricyclo[3.3.1.1$^{3,7}$]decane dihydrogen citrate monohydrate, wherein the condition or disorder is selected from a group of disorders where both α7 and α4β2 nicotinic receptors are implicated. These include attention deficit disorder, attention deficit hyperactivity disorder (ADHD), Alzheimer's disease (AD), mild cognitive impairment, schizophrenia, senile dementia, AIDS dementia, Pick's disease, dementia associated with Lewy bodies, dementia associated with Down's syndrome, amyotrophic lateral sclerosis, Huntington's disease, inflammation, arthritis of various types, smoking cessation, nicotinic withdrawal syndrome, traumatic brain injury, acute pain, post-surgical pain, osteoarthritic pain, neuropathic and inflammatory chronic pain states.

Compounds for the method of the invention, including but not limited to those specified in the examples or otherwise specifically named, can modulate, and often possess an affinity for, nAChRs, and more particularly α7 nAChRs. As α7 nAChRs ligands, the compounds of the invention can be useful for the treatment or prevention of a number of α7 nAChR-mediated diseases or conditions. Certain compounds of the invention includes, in addition to affinity for α7 nAChRs, affinity for α4β2 nAChRs.

For example, α7 nAChRs have been shown to play a significant role in enhancing cognitive function, including aspects of learning, memory and attention (Levin, E. D., J. Neurobiol. 53: 633-640, 2002). As such, α7 ligands are suitable for the treatment of conditions and disorders related to memory and/or cognition including, for example, attention deficit disorder, attention deficit hyperactivity disorder (ADHD), Alzheimer's disease (AD), mild cognitive impairment, senile dementia, AIDS dementia, Pick's disease, dementia associated with Lewy bodies, and dementia associated with Down's syndrome, as well as cognitive deficits associated with schizophrenia.

In addition, α7-containing nAChRs have been shown to be involved in the cytoprotective effects of nicotine both in vitro (Jonnala, R. B. and Buccafusco, J. J., J. Neurosci. Res. 66: 565-572, 2001) and in vivo (Shimohama, S. et al., Brain Res. 779: 359-363, 1998). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 nAChRs by β-amyloid peptides linked to Alzheimer's disease has been implicated as a key factor in development of the cognitive deficits associated with the disease (Liu, Q.-S., Kawai, H., Berg, D. K., PNAS 98: 4734-4739, 2001). α7 selective ligands can influence neuroprotective pathways leading to decreased phosphorylation of the tau protein, whose hyperphosphorylation is required for neurofibrillary tangle formation in various tau related pathologies such as Alzheimer's disease and various other dementias (Bitner et al., Soc. Neuroscience, 2006 abst 325.6). The activation of α7 nAChRs has been shown to block this neurotoxicity (Kihara, T. et al., J. Biol. Chem. 276: 13541-13546, 2001). As such, selective ligands that enhance α7 activity can counter the deficits of Alzheimer's and other neurodegenerative diseases.

Alpha-7 nAChRs also have been implicated in aspects of neurodevelopment, for example neurogenesis of the brain. (Falk, L. et al., Developmental Brain Research 142:151-160, 2003; Tsuneki, H., et al., J. Physiol. (London) 547:169-179, 2003; Adams, C. E., et al., Developmental Brain Research 139:175-187, 2002). As such, α7 nAChRs can be useful in preventing or treating conditions or disorders associated with impaired neurodevelopment, for example schizophrenia. (Sawa A., Mol. Med. 9:3-9, 2003).

Several compounds with high affinity for α4β2 neuronal nicotinic receptors (NNRs) have been shown to improve attentive and cognitive performance in preclinical models that are relevant to attention-deficit/hyperactivity disorder (ADHD), a disease characterized by core symptoms of hyperactivity, inattentiveness, and impulsivity. For example, ABT-418, a full agonist at α4β2 NNRs is efficacious in a variety of preclinical cognition models. ABT-418 administered transdermally, was shown in a controlled clinical trial in 32 adults to be effective in treating ADHD in general, and attentional/cognitive deficits in particular (Wilens, T. E.; Biederman, J.; Spencer, T. J.; Bostic, J.; Prince, J.; Monuteaux, M. C.; Soriano, J.; Fince, C.; Abrams, A.; Rater, M.; Polisner, D. The American Journal of Psychiatry (1999) 156(12), 1931-1937.). Likewise, ABT-418 showed a signal of efficacy in a pilot Alzheimer's disease trial. ABT-089, a α4β2 selective partial agonist, has been shown in rodent and primate animal models to improve attention, learning, and memory deficits. ABT-089 and another α4β2 agonist, ispronicline has shown efficacy in a pilot clinical trials. In addition to cognition, compounds that interact with α4β2 nAChRs such as ABT-594 and others are also efficacious in preclinical and clinical models of pain. As such, ligands that modulate both α7 and α4β2 activity can have broader spectrum of therapeutic efficacy in disease states such as those involving cognitive and attentive deficits, pain, neurodegenerative diseases and others.

Schizophrenia is a complex disease that is characterized by abnormalities in perception, cognition, and emotions. Significant evidence implicates the involvement of α7 nAChRs in this disease, including a measured deficit of these receptors in post-mortem patients (Sawa A., Mol. Med. 9:3-9, 2003; Leonard, S. Eur. J. Pharmacol. 393: 237-242, 2000). Deficits in sensory processing (gating) are one of the hallmarks of schizophrenia. These deficits can be normalized by nicotinic ligands that operate at the α7 nAChR (Adler L. E. et al., Schizophrenia Bull. 24: 189-202, 1998; Stevens, K. E. et al., Psychopharmacology 136: 320-327, 1998). More recent studies have shown that α4β2 nicotinic receptor stimulation also contributes to the effects of nicotine in the DBA/2 mouse model of sensory gating (Radek et al., Psychopharmacology (Berl). 2006 187:47-55. Thus, α7 and α7/α4β2 ligands demonstrate potential in the treatment schizophrenia.

Angiogenesis, a process involved in the growth of new blood vessels, is important in beneficial systemic functions, such as wound healing, vascularization of skin grafts, and enhancement of circulation, for example, increased circulation around a vascular occlusion. Non-selective nAChR agonists like nicotine have been shown to stimulate angiogenesis (Heeschen, C. et al., Nature Medicine 7: 833-839, 2001). Improved angiogenesis has been shown to involve activation of the α7 nAChR (Heeschen, C. et al., J. Clin. Invest. 110: 527-536, 2002). For example, improved conditions related to inflammation, ischemia, cardiac ischemia, and wound healing, for example in diabetic persons, have been associated with α7 nAChR activity (Jacobi, J., et al., Am. J. Pathol. 161:97-104, 2002). Therefore, nAChR ligands that are selective for the α7 subtype offer improved potential for stimulating angiogenesis with an improved side effect profile.

A population of α7 or α4β2 nAChRs in the spinal cord modulate neurotransmission transmission that have been associated with the pain-relieving effects of nicotinic compounds (Cordero-Erausquin, M. and Changeux, J.-P. PNAS 98:2803-2807, 2001). The α7 nAChR or and α7/α4β2 ligands demonstrate therapeutic potential for the treatment of pain states, including acute pain, post-surgical pain, as well as chronic pain states including inflammatory pain and neuropathic pain. Moreover, α7 nAChRs are expressed on the surface of primary macrophages that are involved in the inflammation response, and that activation of the α7 receptor inhibits release of TNF and other cytokines that trigger the inflammation response (Wang, H. et al Nature 421: 384-388, 2003). Therefore, selective α7 ligands demonstrate potential for treating conditions involving inflammation including those associated with various forms of arthritis.

The mammalian sperm acrosome reaction is an exocytosis process important in fertilization of the ovum by sperm. Activation of an α7 nAChR on the sperm cell has been shown to be essential for the acrosome reaction (Son, J. H. and Meizel, S. Biol. Reproduct. 68: 1348-1353 2003). Consequently, selective α7 agents demonstrate utility for treating fertility disorders.

Compounds of the invention are particularly useful for treating and preventing a condition or disorder affecting memory, cognition, neurodegeneration, neurodevelopment, and schizophrenia.

Cognitive impairment associated with schizophrenia often limits the ability of patients to function normally, a symptom not adequately treated by commonly available treatments, for example, treatment with an atypical antipsychotic. (Rowley, M. et al., J. Med. Chem. 44: 477-501, 2001). Such cognitive deficit has been linked to dysfunction of the nicotinic cholinergic system, in particular with decreased activity at α7 receptors. (Friedman, J. I. et al., Biol Psychiatry, 51: 349-357, 2002). Thus, activators of α7 receptors can provide useful treatment for enhancing cognitive function in schizophrenic patients who are being treated with atypical antipsychotics. Accordingly, the combination of an α7 nAChR ligand and an atypical antipsychotic would offer improved therapeutic utility. Specific examples of suitable atypical antipsychotics include, but are not limited to, clozapine, risperidone, olanzapine, quetiapine, ziprasidone, zotepine, iloperidone, and the like.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in a pharmaceutically acceptable salt, ester, amide, or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 μg/kg body weight to about 10 mg/kg body weight. More preferable doses can be in the range of from about 0.10 μg/kg body weight to about 1 mg/kg body weight. If desired, the effective daily dose can be divided into multiple doses for purposes of administration. Consequently, single dose compositions may contain such amounts or submultiples thereof to make up the daily dose.

By way of example, and not of limitation, examples of the present invention shall now be given.

EXAMPLE 1

(4s)-4-(5-phenyl-1,3,4-thiadiazol-2-yloxy)-1-azatricyclo[3.3.1.1$^{3,7}$]decane free base To prepare a (4s)-4-(5-phenyl-1,3,4-thiadiazol-2-yloxy)-1-azatricyclo[3.3.1.1$^{3,7}$]decane free base single crystal, (4s)-4-(5-phenyl-1,3,4-thiadiazol-2-yloxy)-1-azatricyclo [3.3.1.1$^{3,7}$]decane free base (13 mg) was dissolved in 1.0 mL of 2-propanol. The solvent was allowed evaporate slowly. Single crystals of (4s)-4-(5-phenyl-1,3,4-thiadiazol-2-yloxy)-1-azatricyclo[3.3.1.1$^{3,7}$]decane free base formed over time.

EXAMPLE 2

(4s)-4-(5-phenyl-1,3,4-thiadiazol-2-yloxy)-1-azatricyclo[3.3.1.1$^{3,7}$]decane dihydrogen citrate In order to produce the crystalline monohydrate form, it is important to first develop the anhydrous salt form of the compound. As such, this example is directed to the process for creating the anhydrous dihydrogen citrate salt. (4s)-4-(5-phenyl-1,3,4-thiadiazol-2-yloxy)-1-azatricyclo[3.3.1.1$^{3,7}$]decane free base (63 mg, 0.2 mmol) was dissolved in 1.0 mL of methanol. Citric acid (41 mg, 0.21 mmol) was dissolved in 0.5 mL of methanol. The citric acid solution was added to the (4s)-4-(5-phenyl-1,3,4-thiadiazol-2-yloxy)-1-azatricyclo[3.3.1.1$^{3,7}$]decane freebase solution while stirring. The vial was removed from the stir plate after the addition, and the solvent allowed to evaporate slowly. (4s)-4-(5-phenyl-1,3,4-thiadiazol-2-yloxy)-1-azatricyclo[3.3.1.1$^{3,7}$]decane dihydrogen citrate crystallized over time.

To prepare a (4s)-4-(5-phenyl-1,3,4-thiadiazol-2-yloxy)-1-azatricyclo[3.3.1.1$^{3,7}$]decane dihydrogen citrate single crystal, (4s)-4-(5-phenyl-1,3,4-thiadiazol-2-yloxy)-1-azatricyclo[3.3.1.1$^{3,7}$]decane dihydrogen citrate (20 mg) was dissolved in 0.8 mL water/2-propanol (1:6, V/V) at 50° C. The solution was seeded with (4s)-4-(5-phenyl-1,3,4-thiadiazol-2-yloxy)-1-azatricyclo[3.3.1.1$^{3,7}$]decane dihydrogen citrate solid and allowed to cool to ambient temperatures in a sealed vial. Single crystals formed over time.

EXAMPLE 3

(4s)-4-(5-phenyl-1,3,4-thiadiazol-2-yloxy)-1-azatricyclo[3.3.1.1$^{3,7}$]decane dihydrogen citrate monohydrate The monohydrate salt may be formed in accordance with the following procedure. First, the (4s)-4-(5-phenyl-1,3,4-thiadiazol-2-yloxy)-1-azatricyclo[3.3.1.1$^{3,7}$]decane dihydrogen citrate anhydrate is dissolved in 4 volumes of 2-propanol and 1 volume of water, at a temperature of 75° C. The temperature of the resulting solvent is then adjusted to 65° C. over a period of time of no less than 30 minutes. Once the resulting solution reaches 65° C., 6 volumes of 2-propanol are added to the solution and mixed for a period of no less than 30 minutes. Upon mixing, spontaneous nucleation of the solution occurs, and the temperature of the resulting slurry is slowly decreased to 40° C. over a period of greater than 2 hours. After the slurry reaches a temperature of 40° C., 5 volumes of 2-propanol are added to the slurry over a period of no less than 3 hours. After addition of the 2-propanol to the slurry, the resulting slurry is held at a temperature of 40° C. for a period of at least 1 hour. Subsequently, the temperature of the slurry is slowly adjusted to 5° C. and mixed at 5° C. for at least 1 hour. After these steps are completed, the monohydrate solids are harvested by means of filtration.

EXAMPLE 4

Formation of (4s)-4-(5-phenyl-1,3,4-thiadiazol-2-yloxy)-1-azatricyclo[3.3.1.1$^{3,7}$]decane dihydrogen citrate monohydrate The inventors produced (4s)-4-(5-phenyl-1,3,4-thiadiazol-2-yloxy)-1-azatricyclo[3.3.1.1$^{3,7}$]decane dihydrogen citrate monohydrate crystals according to the following procedure. First, 200 mg of the (4s)-4-(5-phenyl-1,3,4-thiadiazol-2-yloxy)-1-azatricyclo[3.3.1.1$^{3,7}$]decane dihydrogen citrate anhydrate solid were suspended in approximately 1.0 mL of water. Subsequently the suspension was sealed with parafilm and stored in a cabinet, protected from light conditions, at ambient conditions for a sufficient time to allow crystallization. After crystal formation, the inventors tested the crystals by single crystal X-ray diffraction, and determined that the crystal product was (4s)-4-(5-phenyl-1,3,4-thiadiazol-2-yloxy)-1-azatricyclo[3.3.1.1$^{3,7}$]decane dihydrogen citrate monohydrate.

EXAMPLE 5

(4s)-4-(5-phenyl-1,3,4-thiadiazol-2-yloxy)-1-azatricyclo[3.3.1.1$^{3,7}$]decane dihydrogen citrate monohydrate The inventors produced (4s)-4-(5-phenyl-1,3,4-thiadiazol-2-yloxy)-1-azatricyclo[3.3.1.1$^{3,7}$]decane dihydrogen citrate monohydrate crystals according to the following procedure. The anhydrate solid of (4s)-4-(5-phenyl-1,3,4-thiadiazol-2-yloxy)-1-azatricyclo[3.3.1.1$^{3,7}$]decane dihydrogen citrate was suspended in a mixture of an organic solvent (e.g., methanol, ethanol, acetonitrile, etc.) and water. After equilibrating the suspension at ambient conditions, the anhydrate compound converted to the monohydrate compound. Subsequently, the inventors extracted the monohydrate compound by means of filtration and confirmed the monohydrate structure by X-ray diffraction.

EXAMPLE 6

Determination of Critical Water Activity for Hydrate Formation of (4s)-4-(5-phenyl-1,3,4-thiadiazol-2-yloxy)-1-azatricyclo[3.3.1.1$^{3,7}$]decane dihydrogen citrate The inventors determined the critical water activity for (4s)-4-(5-phenyl-1,3,4-thiadiazol-2-yloxy)-1-azatricyclo[3.3.1.1$^{3,7}$]decane dihydrogen citrate monohydrate at ambient temperature. Specifically, the inventors developed suspensions of the crystalline product in mixtures of methanol and water, with water activities of 0.20, 0.15, 0.10, and 0.05, performing powder X-ray diffraction patterns for each suspension, respectively. The inventors also incorporated the powder X-ray diffraction pattern for substantially pure crystalline monohydrate salt, and substantially pure crystalline anhydrous salt, and incorporated all powder X-ray diffraction data onto a single overlay graph. The inventors incorporated the data onto a single graph to determine the water activity point (or range of points) at which the anhydrous form converts to the monohydrate form.

Figure 4A:
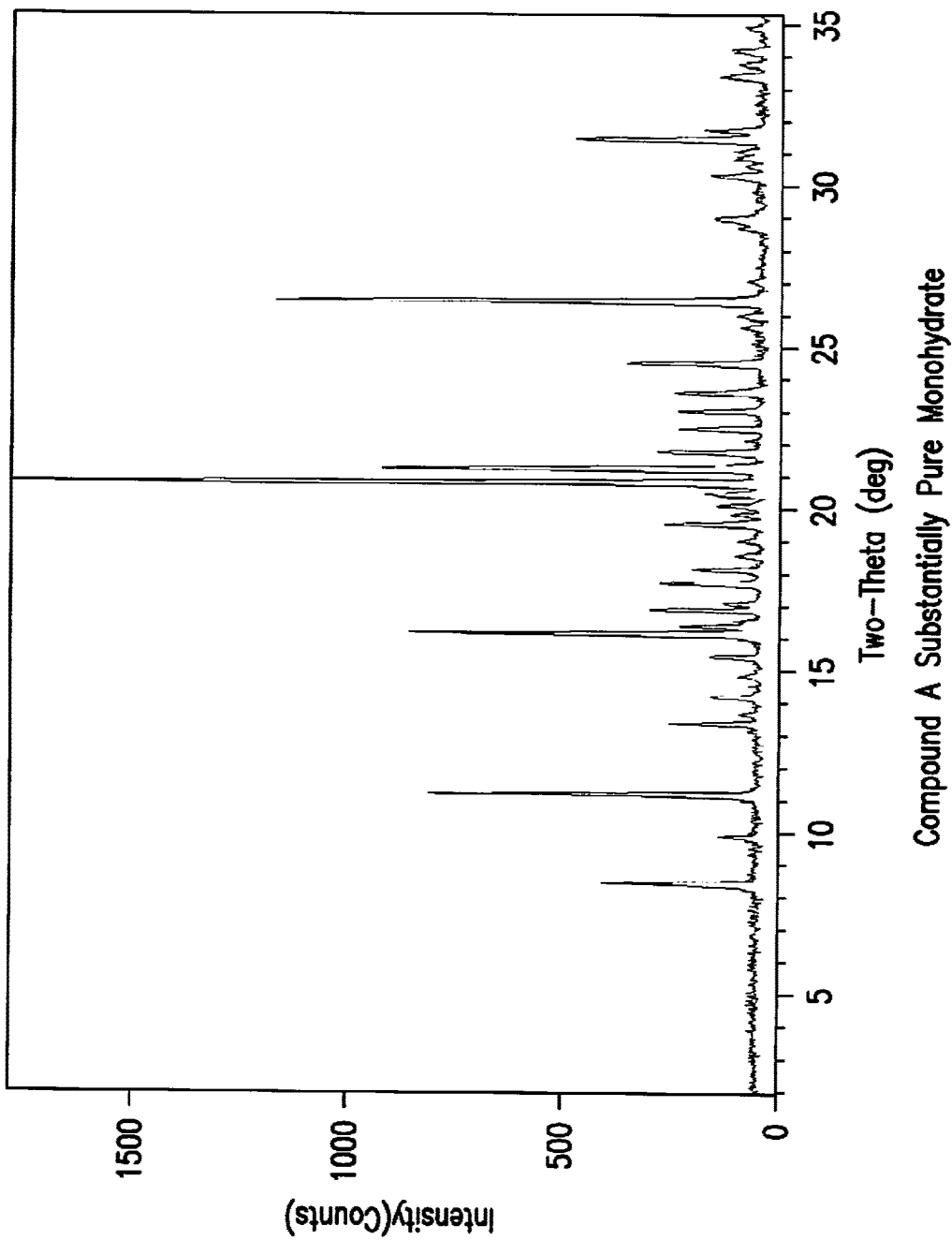
FIG. 4(a) illustrates the X-ray powder diffraction pattern for a formulation consisting of substantially pure crystalline monohydrate (4s)-4-(5-phenyl-1,3,4-thiadiazol-2-yloxy)-1-azatricyclo[3.3.1.1$^{3,7}$]decane dihydrogen citrate (Compound A).
Figure 4D:
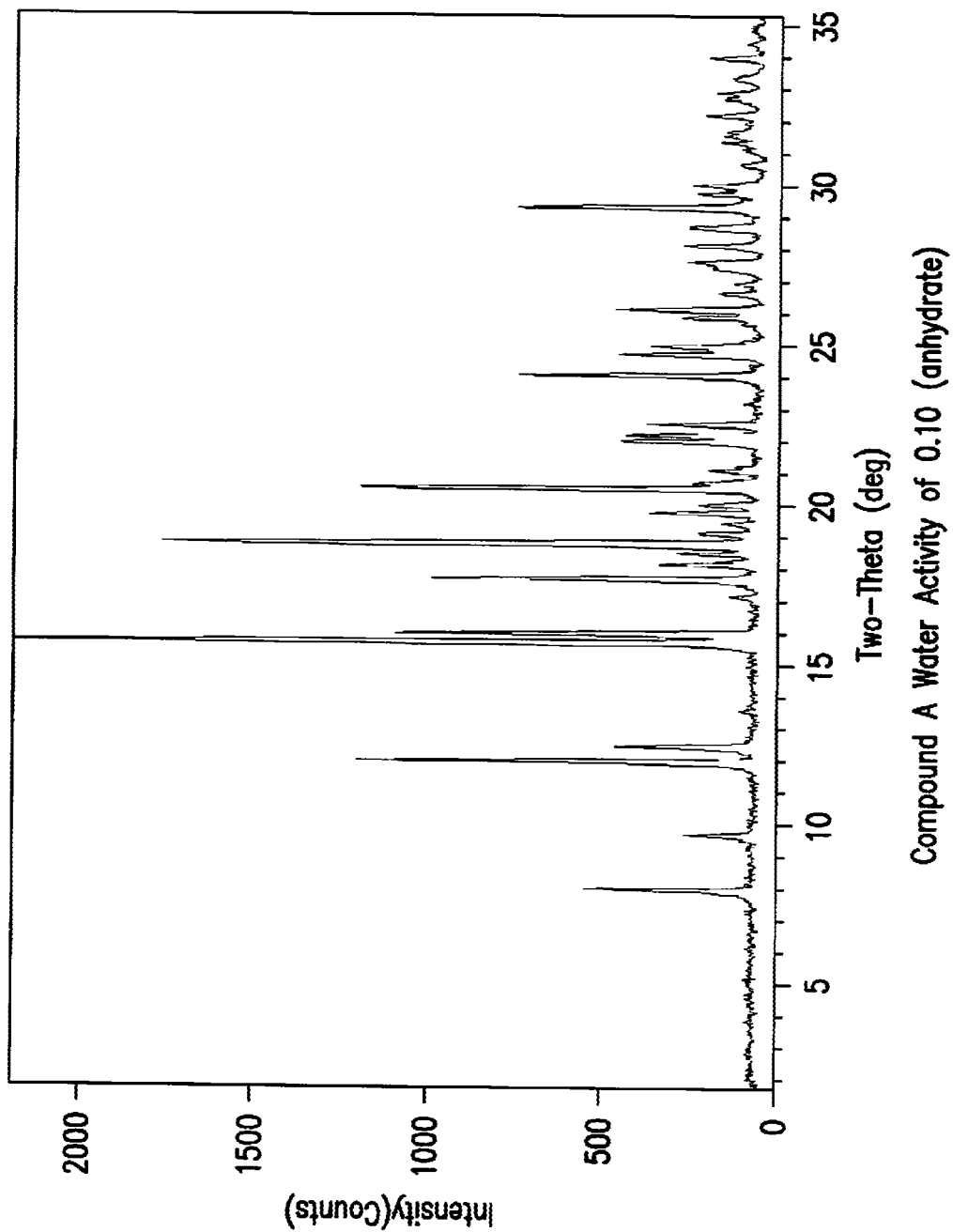
FIG. 4(d) illustrates the X-ray powder diffraction pattern for a (4s)-4-(5-phenyl-1,3,4-thiadiazol-2-yloxy)-1-azatricyclo[3.3.1.1$^{3,7}$]decane dihydrogen citrate (Compound A) solid recovered from a suspension having a water activity of 0.10.
Figure 4F:
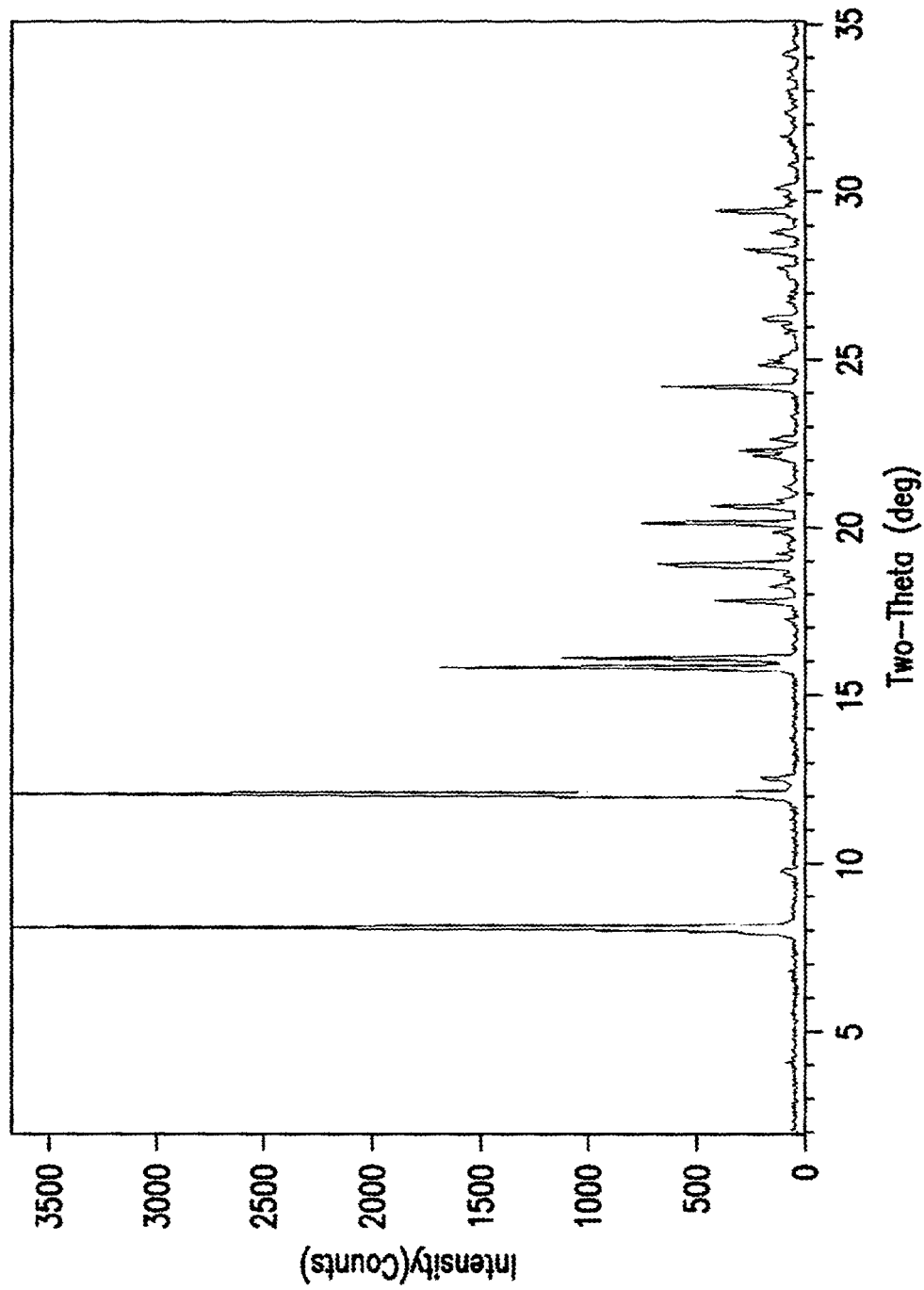
FIG. 4(f) illustrates the X-ray powder diffraction pattern for a formulation consisting of substantially pure crystalline anhydrous (4s)-4-(5-phenyl-1,3,4-thiadiazol-2-yloxy)-1-azatricyclo[3.3.1.1$^{3,7}$]decane dihydrogen citrate (Compound A).

FIGS. 4(a)-4(f) illustrate the X-ray powder diffraction data for six different formulations. FIG. 4(a) illustrates the X-ray powder diffraction pattern for a formulation consisting of substantially pure crystalline monohydrate (4s)-4-(5-phenyl-1,3,4-thiadiazol-2-yloxy)-1-azatricyclo[3.3.1.1$^{3,7}$]decane dihydrogen citrate. FIG. 4(b) illustrates the X-ray powder diffraction pattern for a (4s)-4-(5-phenyl-1,3,4-thiadiazol-2-yloxy)-1-azatricyclo[3.3.1.1$^{3,7}$]decane dihydrogen citrate solid recovered from a suspension having a water activity of 0.20. FIG. 4(c) illustrates the X-ray powder diffraction pattern for a (4s)-4-(5-phenyl-1,3,4-thiadiazol-2-yloxy)-1-azatricyclo[3.3.1.1$^{3,7}$]decane dihydrogen citrate solid recovered from a suspension having a water activity of 0.15. FIG. 4(d) illustrates the X-ray powder diffraction pattern for a (4s)-4-(5-phenyl-1,3,4-thiadiazol-2-yloxy)-1-azatricyclo[3.3.1.1$^{3,7}$]decane dihydrogen citrate solid recovered from a suspension having a water activity of 0.10. FIG. 4(e) illustrates the X-ray powder diffraction pattern for a (4s)-4-(5-phenyl-1,3,4-thiadiazol-2-yloxy)-1-azatricyclo[3.3.1.1$^{3,7}$]decane dihydrogen citrate solid recovered from a suspension having a water activity of 0.05. FIG. 4(f) illustrates the X-ray powder diffraction pattern for a formulation consisting of substantially pure crystalline anhydrous (4s)-4-(5-phenyl-1,3,4-thiadiazol-2-yloxy)-1-azatricyclo[3.3.1.1$^{3,7}$]decane dihydrogen citrate.

Comparison of FIGS. 4(c) and 4(d) reveals a shift in the X-ray diffraction pattern indicative of a monohydrate to an X-ray diffraction pattern indicative of an anhydrate. The pattern illustrated in FIGS. 4(c) and 4(d) represent the solids collected from the suspensions having water activities of 0.15 and 0.10, respectively. Therefore, one skilled in the art will appreciate that when the water activity of the solvent used to crystallize the (4s)-4-(5-phenyl-1,3,4-thiadiazol-2-yloxy)-1-azatricyclo[3.3.1.1$^{3,7}$]decane dihydrogen citrate, is 0.15 or greater, the (4s)-4-(5-phenyl-1,3,4-thiadiazol-2-yloxy)-1-azatricyclo[3.3.1.1$^{3,7}$]decane dihydrogen citrate will exist as the monohydrate salt. However, if the solvent comprises a water activity of 0.10 or less, the (4s)-4-(5-phenyl-1,3,4-thiadiazol-2-yloxy)-1-azatricyclo[3.3.1.1$^{3,7}$]decane dihydrogen citrate will exist as the anhydrate.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A pharmaceutical composition comprising the crystalline monohydrate of (4s)-4-(5-phenyl-1,3,4-thiadiazol-2-yloxy)-1-azatricyclo[3.3.1.1$^{3,7}$]decane dihydrogen citrate as an active ingredient and a pharmaceutically acceptable carrier, diluent, or excipient.

2. The pharmaceutical composition of claim 1, wherein the crystalline monohydrate of (4s)-4-(5-phenyl-1,3,4-thiadiazol-2-yloxy)-1-azatricyclo[3.3.1.1$^{3,7}$]decane dihydrogen citrate is present in an amount ranging from approximately 0.1% to approximately 99.9% by weight based on the total weight of the composition.

3. The pharmaceutical composition of claim 1, wherein the crystalline monohydrate of (4s)-4-(5-phenyl-1,3,4-thiadiazol-2-yloxy)-1-azatricyclo[3.3.1.1$^{3,7}$]decane dihydrogen citrate demonstrates characteristic peaks in the powder X-ray diffraction pattern at values in degrees two theta of 8.4±0.20, 11.3±0.20, 15.5±0.20, and 20.7±0.20.

* * * * *